United States Patent
Lv et al.

(10) Patent No.: US 11,891,423 B2
(45) Date of Patent: Feb. 6, 2024

(54) FUSION PROTEIN BINDING TO CD47 PROTEIN AND APPLICATION THEREOF

(71) Applicants: HANGZHOU SUMGEN BIOTECH CO., LTD., Zhejiang (CN); SUMGEN MAB (BEIJING) BIOTECH CO., LTD., Beijing (CN)

(72) Inventors: Ming Lv, Zhejiang (CN); Xiaoran Ding, Zhejiang (CN); Shiwei Miao, Zhejiang (CN); Bin Tan, Zhejiang (CN); Xuegong Wang, Zhejiang (CN)

(73) Assignees: HANGZHOU SUMGEN BIOTECH CO., LTD., Zhejiang (CN); SUMGEN MAB (BEIJING) BIOTECH CO., LTD., Beijing (CN)

( * ) Notice: Subject to any disclaimer, the term of this patent is extended or adjusted under 35 U.S.C. 154(b) by 41 days.

(21) Appl. No.: 17/048,202

(22) PCT Filed: Apr. 16, 2019

(86) PCT No.: PCT/CN2019/082863
§ 371 (c)(1),
(2) Date: Oct. 16, 2020

(87) PCT Pub. No.: WO2019/201236
PCT Pub. Date: Oct. 24, 2019

(65) Prior Publication Data
US 2021/0171593 A1 Jun. 10, 2021

(30) Foreign Application Priority Data
Apr. 17, 2018 (CN) .......................... 201810343482.9

(51) Int. Cl.
| | |
|---|---|
| C07K 16/46 | (2006.01) |
| C07K 19/00 | (2006.01) |
| C07K 14/00 | (2006.01) |
| A61K 39/395 | (2006.01) |
| C07K 14/47 | (2006.01) |
| A61P 35/00 | (2006.01) |
| A61K 38/00 | (2006.01) |
| A61K 39/00 | (2006.01) |

(52) U.S. Cl.
CPC .......... *C07K 14/4703* (2013.01); *A61P 35/00* (2018.01); *A61K 38/00* (2013.01); *A61K 39/395* (2013.01); *A61K 2039/505* (2013.01); *C07K 16/46* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2017/0107270 A1*  4/2017  Pons ....................... A61P 37/02

FOREIGN PATENT DOCUMENTS

| | | | |
|---|---|---|---|
| CN | 105073780 A | 11/2015 | |
| CN | 106146670 A | 11/2016 | |
| CN | 107108748 A | 8/2017 | |
| WO | 2010070047 A1 | 6/2010 | |
| WO | 2014094122 A1 | 6/2014 | |
| WO | WO-2015066557 A1 * | 5/2015 | ............... C12N 9/22 |
| WO | 2016024021 A1 | 2/2016 | |
| WO | 2017027422 A1 | 2/2017 | |
| WO | WO-2019023347 A1 * | 1/2019 | ......... A61K 39/3955 |

OTHER PUBLICATIONS

Tokuriki et al., Stability effects of mutations and protein evolvability. Curr. Opin. Struc. Biol. 19:596-604; (2009). (Year: 2009).*
Fenton et al. Rheostat positions: A new classification of protein positions relevant to pharmacogenomics Medicinal Chemistry Research 29:1133-1146; (2020). (Year: 2020).*
Bhattacharya et al. Bhattacharya et al. Impact of genetic variation on three dimensional structure and function of proteins PLoS ONE 12(3): e0171355; (2017). (Year: 2017).*
Gua et al. Protein tolerance to random amino acid change. PNAS USA 101(25):9205-10; (2004). (Year: 2004).*
PCT/CN2019/082863 International Search Report dated Jul. 19, 2019.
Lee, Winston Y., et al., Novel Structural Determinants on SIRPa that Mediate Binding to CD47, J of Immunology, 2007; 179; 7741-7750.
Petrova, Penka S., et al., TTI-621 (SIRPαFc): a CD47-Blocking Innate Immune Checkpoint Inhibitor with Broad Antitumor Activity and Minimal Erythrocyte Binding, Clinical Cancer Research, 23(4), pp. 1068-1079, Feb. 15, 2017.
Weiskopf, Kipp, et al., Engineered SIRPα variants as immunotherapeutic adjuvants to anti-cancer antibodies, NIH Public Access, Science, author manuscript, 341(6141), Jul. 5, 2013.

* cited by examiner

*Primary Examiner* — Elizabeth C. Kemmerer
*Assistant Examiner* — Regina M DeBerry
(74) *Attorney, Agent, or Firm* — Honigman LLP; Thomas A. Wootton, Esq.; Jonathan P. O'Brien

(57) ABSTRACT

Provided by the present invention are a fusion protein binding to a CD47 protein and an application thereof, wherein the fusion protein is capable of binding to a CD47 protein by using a KD value of $1\times10^{-8}$M or lower. The fusion protein may specifically block the interaction between a CD47 protein and SIRPα without causing a blood coagulation reaction, and may further inhibit the growth and/or proliferation of tumors or tumor cells.

9 Claims, 16 Drawing Sheets

Specification includes a Sequence Listing.

SEQUENCE LISTING

<160> NUMBER OF SEQ ID NOS: 68

<210> SEQ ID NO 1
<211> LENGTH: 117
<212> TYPE: PRT
<213> ORGANISM: Artificial Sequence
<220> FEATURE:
<223> OTHER INFORMATION: M1

<400> SEQUENCE: 1

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Ile Leu Ile Tyr
        35                  40                  45

Asn Gln Lys Lys Gly His Phe Pro Arg Val Thr Thr Leu Ser Asp Ser
    50                  55                  60

-continued

Thr Arg Arg Gly Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                 85                  90                  95

Pro Asp Asp Leu Glu Phe Lys Ser Gly Ala Gly Thr Glu Leu Ser Val
            100                 105                 110

Arg Ala Lys Pro Ser
        115

<210> SEQ ID NO 2
<211> LENGTH: 117
<212> TYPE: PRT
<213> ORGANISM: Artificial Sequence
<220> FEATURE:
<223> OTHER INFORMATION: M5

<400> SEQUENCE: 2

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Val Pro Val Gly
                 20                  25                  30

Pro Ile Gln Trp Phe Arg Gly Ala Gly Pro Gly Arg Asn Leu Ile Tyr
             35                  40                  45

Asn Ser Arg His Gly His Phe Pro Arg Val Thr Thr Val Ser Asp Leu
         50                  55                  60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                 85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 3
<211> LENGTH: 117
<212> TYPE: PRT
<213> ORGANISM: Artificial Sequence
<220> FEATURE:
<223> OTHER INFORMATION: M12

<400> SEQUENCE: 3

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Phe Pro Ile Gly
                 20                  25                  30

Pro Ile Gln Trp Phe Arg Gly Ala Gly Pro Gly Arg Glu Leu Ile Tyr
             35                  40                  45

Asn Gln Arg Lys Gly His Phe Pro Arg Val Thr Thr Val Ser Asp Leu
         50                  55                  60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                 85                  90                  95

```
Pro Asp Asp Ile Glu Phe Lys Ser Gly Ala Gly Thr Glu Leu Ser Val
            100                 105                 110

Arg Ala Lys Pro Ser
        115

<210> SEQ ID NO 4
<211> LENGTH: 117
<212> TYPE: PRT
<213> ORGANISM: Artificial Sequence
<220> FEATURE:
<223> OTHER INFORMATION: M35

<400> SEQUENCE: 4

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Val Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115

<210> SEQ ID NO 5
<211> LENGTH: 117
<212> TYPE: PRT
<213> ORGANISM: Artificial Sequence
<220> FEATURE:
<223> OTHER INFORMATION: M37

<400> SEQUENCE: 5

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Lys Leu Ile Tyr
        35                  40                  45

Asn Gln Arg Asp Gly His Phe Pro Arg Val Thr Thr Val Ser Asp Leu
    50                  55                  60

Thr Lys Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 6
<211> LENGTH: 117
<212> TYPE: PRT
<213> ORGANISM: Artificial Sequence
```

```
<220> FEATURE:
<223> OTHER INFORMATION: M41

<400> SEQUENCE: 6

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
                20                  25                  30

Pro Ile Gln Trp Phe Arg Gly Ala Gly Pro Gly Arg His Leu Ile Tyr
            35                  40                  45

Asn Arg Arg His Gly His Phe Pro Arg Val Thr Thr Val Ser Asp Leu
        50                  55                  60

Thr Lys Arg Asn Asn Met Asp Phe Ser Ile Ser Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 7
<211> LENGTH: 117
<212> TYPE: PRT
<213> ORGANISM: Artificial Sequence
<220> FEATURE:
<223> OTHER INFORMATION: M57

<400> SEQUENCE: 7

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30

Pro Ile Gln Trp Phe Arg Gly Ala Gly Pro Gly Arg Ile Leu Ile Tyr
            35                  40                  45

Asn Gly Lys Arg Gly His Phe Pro Arg Val Thr Thr Leu Ser Asp Thr
        50                  55                  60

Thr Lys Arg Gly Asn Met Asp Phe Ser Ile Ser Ile Arg Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Arg Glu Phe Lys Ser Gly Ala Gly Thr Glu Leu Ser Val
            100                 105                 110

Arg Ala Lys Pro Ser
        115

<210> SEQ ID NO 8
<211> LENGTH: 117
<212> TYPE: PRT
<213> ORGANISM: Artificial Sequence
<220> FEATURE:
<223> OTHER INFORMATION: M67

<400> SEQUENCE: 8

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30
```

```
Pro Ile Gln Trp Phe Arg Gly Ala Gly Pro Gly Arg Met Leu Ile Tyr
            35                  40                  45

Asn Gly Arg Asp Gly His Phe Pro Arg Val Thr Thr Val Ser Asp Leu
 50                      55                  60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
            115

<210> SEQ ID NO 9
<211> LENGTH: 117
<212> TYPE: PRT
<213> ORGANISM: Artificial Sequence
<220> FEATURE:
<223> OTHER INFORMATION: M81

<400> SEQUENCE: 9

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Leu Pro Val Gly
                20                  25                  30

Pro Ile Gln Trp Phe Arg Gly Ala Gly Pro Gly Arg Glu Leu Ile Tyr
            35                  40                  45

Asn Gln Lys Glu Gly His Phe Pro Arg Val Thr Thr Val Ser Asp Leu
 50                      55                  60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
            115

<210> SEQ ID NO 10
<211> LENGTH: 117
<212> TYPE: PRT
<213> ORGANISM: Artificial Sequence
<220> FEATURE:
<223> OTHER INFORMATION: M82

<400> SEQUENCE: 10

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Phe Pro Val Gly
                20                  25                  30

Pro Ile Gln Trp Phe Arg Gly Ala Gly Pro Gly Arg Glu Leu Ile Tyr
            35                  40                  45

Asn Gln Lys Glu Gly His Phe Pro Arg Val Thr Thr Val Ser His Ser
 50                      55                  60

Thr Lys Arg Asn Asn Met Asp Phe Ser Ile Arg Ile His Asn Ile Thr
 65                  70                  75                  80

Pro Ala Asp Ala Gly Thr Tyr Tyr Cys Val Lys Phe Arg Lys Gly Ser
                85                  90                  95
```

```
Pro Asp Asp Ser Glu Phe Lys Ser Gly Ala Gly Thr Glu Leu Ser Val
            100                 105                 110

Arg Ala Lys Pro Ser
        115

<210> SEQ ID NO 11
<211> LENGTH: 117
<212> TYPE: PRT
<213> ORGANISM: Artificial Sequence
<220> FEATURE:
<223> OTHER INFORMATION: M84

<400> SEQUENCE: 11

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser His Ser
    50                  55                  60

Thr Arg Arg Asn Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser
        115

<210> SEQ ID NO 12
<211> LENGTH: 117
<212> TYPE: PRT
<213> ORGANISM: Artificial Sequence
<220> FEATURE:
<223> OTHER INFORMATION: M91

<400> SEQUENCE: 12

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Ala Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115

<210> SEQ ID NO 13
<211> LENGTH: 117
<212> TYPE: PRT
```

-continued

```
<213> ORGANISM: Artificial Sequence
<220> FEATURE:
<223> OTHER INFORMATION: M99

<400> SEQUENCE: 13

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
                20                  25                  30

Pro Ile Gln Trp Phe Arg Gly Ala Gly Pro Gly Arg Lys Leu Ile Tyr
            35                  40                  45

Asn Gln Lys Glu Gly His Phe Pro Arg Val Thr Thr Val Ser Asp Ser
        50                  55                  60

Thr Lys Arg Lys Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
        115

<210> SEQ ID NO 14
<211> LENGTH: 117
<212> TYPE: PRT
<213> ORGANISM: Artificial Sequence
<220> FEATURE:
<223> OTHER INFORMATION: M102

<400> SEQUENCE: 14

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
                20                  25                  30

Pro Ile Gln Trp Phe Arg Gly Ala Gly Pro Gly Arg Glu Leu Ile Tyr
            35                  40                  45

Asn Gly Lys Gly Gly His Phe Pro Arg Val Thr Thr Val Ser Arg Ser
        50                  55                  60

Thr Lys Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115

<210> SEQ ID NO 15
<211> LENGTH: 117
<212> TYPE: PRT
<213> ORGANISM: Artificial Sequence
<220> FEATURE:
<223> OTHER INFORMATION: M111

<400> SEQUENCE: 15

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30
```

Pro Ile Gln Trp Phe Arg Gly Ala Gly Pro Gly Arg Leu Ile Tyr
            35                  40                  45

Asn Asn Arg Gly Gly His Phe Pro Arg Val Thr Thr Leu Ser Glu Thr
     50                  55                  60

Thr Arg Arg Asp Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                 85                  90                  95

Pro Asp Asp Leu Glu Phe Lys Ser Gly Ala Gly Thr Glu Leu Ser Val
             100                 105                 110

Arg Ala Lys Pro Ser
            115

<210> SEQ ID NO 16
<211> LENGTH: 117
<212> TYPE: PRT
<213> ORGANISM: Artificial Sequence
<220> FEATURE:
<223> OTHER INFORMATION: M122

<400> SEQUENCE: 16

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Val Pro Val Gly
             20                  25                  30

Pro Ile Gln Trp Phe Arg Gly Ala Gly Pro Gly Arg Asn Leu Ile Tyr
            35                  40                  45

Asn Ser Arg His Gly His Phe Pro Arg Val Thr Thr Ala Ser Asp Leu
     50                  55                  60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                 85                  90                  95

Pro Asp Asp Val Glu Phe Lys Ser Gly Ala Gly Thr Glu Leu Ser Val
             100                 105                 110

Arg Ala Lys Pro Ser
            115

<210> SEQ ID NO 17
<211> LENGTH: 117
<212> TYPE: PRT
<213> ORGANISM: Artificial Sequence
<220> FEATURE:
<223> OTHER INFORMATION: M126

<400> SEQUENCE: 17

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Val Pro Ile Gly
             20                  25                  30

Pro Ile Gln Trp Phe Arg Gly Ala Gly Pro Gly Arg Val Leu Ile Tyr
            35                  40                  45

Asn Gln Arg Asp Gly His Phe Pro Arg Val Thr Thr Val Ser Glu Thr
     50                  55                  60

Thr Arg Arg Glu Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 18
<211> LENGTH: 117
<212> TYPE: PRT
<213> ORGANISM: Artificial Sequence
<220> FEATURE:
<223> OTHER INFORMATION: M130

<400> SEQUENCE: 18

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Val Leu Ile Tyr
        35                  40                  45

Asn Gln Arg Glu Gly His Phe Pro Arg Val Thr Thr Val Ser Glu Ser
50                  55                  60

Thr Arg Arg Asp Asn Met Asp Phe Ser Ile Arg Ile Arg Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 19
<211> LENGTH: 117
<212> TYPE: PRT
<213> ORGANISM: Artificial Sequence
<220> FEATURE:
<223> OTHER INFORMATION: M135

<400> SEQUENCE: 19

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Leu Leu Ile Tyr
        35                  40                  45

Asn Gly Lys Gly Gly His Phe Pro Arg Val Thr Thr Leu Ser Glu Thr
50                  55                  60

Thr Arg Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 20
<211> LENGTH: 117
<212> TYPE: PRT
<213> ORGANISM: Artificial Sequence
<220> FEATURE:
<223> OTHER INFORMATION: M145

<400> SEQUENCE: 20

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Asn Leu Ile Tyr
        35                  40                  45

Asn Gly Lys Gly Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115
```

<210> SEQ ID NO 21
<211> LENGTH: 350
<212> TYPE: PRT
<213> ORGANISM: Artificial Sequence
<220> FEATURE:
<223> OTHER INFORMATION: SS002M1

<400> SEQUENCE: 21

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Ile Leu Ile Tyr
        35                  40                  45

Asn Gln Lys Lys Gly His Phe Pro Arg Val Thr Thr Leu Ser Asp Ser
    50                  55                  60

Thr Arg Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190
```

```
Lys Pro Arg Glu Glu Gln Tyr Asn Ser Thr Tyr Arg Val Val Ser Val
            195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 22
<211> LENGTH: 350
<212> TYPE: PRT
<213> ORGANISM: Artificial Sequence
<220> FEATURE:
<223> OTHER INFORMATION: SS002M5

<400> SEQUENCE: 22

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Asn Leu Ile Tyr
        35                  40                  45

Asn Ser Arg His Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205
```

```
Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
            245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 23
<211> LENGTH: 350
<212> TYPE: PRT
<213> ORGANISM: Artificial Sequence
<220> FEATURE:
<223> OTHER INFORMATION: SS002M12

<400> SEQUENCE: 23

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Ile Gly
            20                  25                  30

Pro Ile Gln Trp Phe Arg Gly Ala Gly Pro Gly Arg Glu Leu Ile Tyr
        35                  40                  45

Asn Gln Arg Lys Gly His Phe Pro Arg Val Thr Thr Val Ser Asp Leu
50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220
```

```
Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
            245                 250                 255

Ser Arg Asp Glu Leu Thr Lys Asn Gln Val Ser Leu Thr Cys Leu Val
        260                 265                 270

Lys Gly Phe Tyr Pro Ser Asp Ile Ala Val Glu Trp Glu Ser Asn Gly
    275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 24
<211> LENGTH: 350
<212> TYPE: PRT
<213> ORGANISM: Artificial Sequence
<220> FEATURE:
<223> OTHER INFORMATION: SS002M35

<400> SEQUENCE: 24

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Val Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240
```

```
Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 25
<211> LENGTH: 350
<212> TYPE: PRT
<213> ORGANISM: Artificial Sequence
<220> FEATURE:
<223> OTHER INFORMATION: SS002M37

<400> SEQUENCE: 25

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Lys Leu Ile Tyr
        35                  40                  45

Asn Gln Arg Asp Gly His Phe Pro Arg Val Thr Thr Val Ser Asp Leu
    50                  55                  60

Thr Lys Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255
```

```
Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 26
<211> LENGTH: 350
<212> TYPE: PRT
<213> ORGANISM: Artificial Sequence
<220> FEATURE:
<223> OTHER INFORMATION: SS002M41

<400> SEQUENCE: 26

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg His Leu Ile Tyr
        35                  40                  45

Asn Arg Arg His Gly His Phe Pro Arg Val Thr Thr Val Ser Asp Leu
    50                  55                  60

Thr Lys Arg Asn Asn Met Asp Phe Ser Ile Ser Ile Ser Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270
```

```
Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 27
<211> LENGTH: 350
<212> TYPE: PRT
<213> ORGANISM: Artificial Sequence
<220> FEATURE:
<223> OTHER INFORMATION: SS002M57

<400> SEQUENCE: 27

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Ile Leu Ile Tyr
        35                  40                  45

Asn Gly Lys Arg Gly His Phe Pro Arg Val Thr Thr Leu Ser Asp Thr
    50                  55                  60

Thr Lys Arg Gly Asn Met Asp Phe Ser Ile Ser Ile Arg Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Arg Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285
```

```
Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 28
<211> LENGTH: 350
<212> TYPE: PRT
<213> ORGANISM: Artificial Sequence
<220> FEATURE:
<223> OTHER INFORMATION: SS002M67

<400> SEQUENCE: 28

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30

Pro Ile Gln Trp Phe Arg Gly Ala Gly Pro Gly Arg Met Leu Ile Tyr
            35                  40                  45

Asn Gly Arg Asp Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300
```

```
Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
            325                 330                 335

Asn His Tyr Thr Gln Lys Ser Leu Ser Leu Ser Pro Gly Lys
            340                 345                 350

<210> SEQ ID NO 29
<211> LENGTH: 350
<212> TYPE: PRT
<213> ORGANISM: Artificial Sequence
<220> FEATURE:
<223> OTHER INFORMATION: SS002M81

<400> SEQUENCE: 29

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320
```

Gln Gln Gly Asn Val Phe Ser Cys Ser Val Met His Glu Ala Leu His
            325                 330                 335

Asn His Tyr Thr Gln Lys Ser Leu Ser Leu Ser Pro Gly Lys
            340                 345                 350

<210> SEQ ID NO 30
<211> LENGTH: 350
<212> TYPE: PRT
<213> ORGANISM: Artificial Sequence
<220> FEATURE:
<223> OTHER INFORMATION: SS002M82

<400> SEQUENCE: 30

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser His Ser
    50                  55                  60

Thr Lys Arg Asn Asn Met Asp Phe Ser Ile Arg Ile Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 31
<211> LENGTH: 350
<212> TYPE: PRT
<213> ORGANISM: Artificial Sequence
<220> FEATURE:
<223> OTHER INFORMATION: SS002M84

<400> SEQUENCE: 31

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser His Ser
    50                  55                  60

Thr Arg Arg Asn Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 32
<211> LENGTH: 350
<212> TYPE: PRT
<213> ORGANISM: Artificial Sequence
<220> FEATURE:
<223> OTHER INFORMATION: SS002M91

<400> SEQUENCE: 32

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Ala Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 33
<211> LENGTH: 350

```
<212> TYPE: PRT
<213> ORGANISM: Artificial Sequence
<220> FEATURE:
<223> OTHER INFORMATION: SS002M99

<400> SEQUENCE: 33

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
                20                  25                  30

Pro Ile Gln Trp Phe Arg Gly Ala Gly Pro Gly Arg Lys Leu Ile Tyr
            35                  40                  45

Asn Gln Lys Glu Gly His Phe Pro Arg Val Thr Thr Val Ser Asp Ser
        50                  55                  60

Thr Lys Arg Lys Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 34
<211> LENGTH: 350
<212> TYPE: PRT
<213> ORGANISM: Artificial Sequence
<220> FEATURE:
```

<223> OTHER INFORMATION: SS002M102

<400> SEQUENCE: 34

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Glu Leu Ile Tyr
        35                  40                  45

Asn Gly Lys Gly Gly His Phe Pro Arg Val Thr Thr Val Ser Arg Ser
    50                  55                  60

Thr Lys Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 35
<211> LENGTH: 350
<212> TYPE: PRT
<213> ORGANISM: Artificial Sequence
<220> FEATURE:
<223> OTHER INFORMATION: SS002M111

-continued

```
<400> SEQUENCE: 35

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Arg Leu Ile Tyr
        35                  40                  45

Asn Asn Arg Gly Gly His Phe Pro Arg Val Thr Thr Leu Ser Glu Thr
    50                  55                  60

Thr Arg Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 36
<211> LENGTH: 350
<212> TYPE: PRT
<213> ORGANISM: Artificial Sequence
<220> FEATURE:
<223> OTHER INFORMATION: SS002M122
```

```
<400> SEQUENCE: 36

Glu Leu Gln Val Ile Gln Pro Asp Lys Ser Val Leu Ala Ala Gly
1               5                   10                  15

Glu Thr Ala Thr Leu Arg Cys Thr Ala Thr Ser Leu Val Pro Val Gly
                20                  25                  30

Pro Ile Gln Trp Phe Arg Gly Ala Gly Pro Gly Arg Asn Leu Ile Tyr
            35                  40                  45

Asn Ser Arg His Gly His Phe Pro Arg Val Thr Thr Ala Ser Asp Leu
        50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
                100                 105                 110

Arg Ala Lys Pro Ser Leu Glu Pro Lys Ser Cys Asp Lys Thr His Thr
            115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
                260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 37
<211> LENGTH: 350
<212> TYPE: PRT
<213> ORGANISM: Artificial Sequence
<220> FEATURE:
<223> OTHER INFORMATION: SS002M126
```

<400> SEQUENCE: 37

| Glu | Leu | Gln | Val | Ile | Gln | Pro | Asp | Lys | Ser | Val | Leu | Val | Ala | Ala | Gly |
|---|---|---|---|---|---|---|---|---|---|---|---|---|---|---|---|
| 1 | | | | 5 | | | | | 10 | | | | | 15 | |

| Glu | Thr | Ala | Thr | Leu | Arg | Cys | Thr | Ala | Thr | Ser | Leu | Val | Pro | Ile | Gly |
| | | | 20 | | | | | 25 | | | | | 30 | | |

| Pro | Ile | Gln | Trp | Phe | Arg | Gly | Ala | Gly | Pro | Gly | Arg | Val | Leu | Ile | Tyr |
| | | | 35 | | | | | 40 | | | | | 45 | | |

| Asn | Gln | Arg | Asp | Gly | His | Phe | Pro | Arg | Val | Thr | Thr | Val | Ser | Glu | Thr |
| | 50 | | | | | 55 | | | | | 60 | | | | |

| Thr | Arg | Arg | Glu | Asn | Met | Asp | Phe | Ser | Ile | Arg | Ile | Gly | Asn | Ile | Thr |
| 65 | | | | | 70 | | | | | 75 | | | | | 80 |

| Pro | Ala | Asp | Ala | Gly | Thr | Tyr | Tyr | Cys | Val | Lys | Phe | Arg | Lys | Gly | Ser |
| | | | | 85 | | | | | 90 | | | | | 95 | |

| Pro | Asp | Asp | Val | Glu | Phe | Lys | Ser | Gly | Ala | Gly | Thr | Glu | Leu | Ser | Val |
| | | | 100 | | | | | 105 | | | | | 110 | | |

| Arg | Ala | Lys | Pro | Ser | Leu | Glu | Pro | Lys | Ser | Cys | Asp | Lys | Thr | His | Thr |
| | | 115 | | | | | 120 | | | | | 125 | | | |

| Cys | Pro | Pro | Cys | Pro | Ala | Pro | Glu | Leu | Leu | Gly | Gly | Pro | Ser | Val | Phe |
| 130 | | | | | 135 | | | | | 140 | | | | | |

| Leu | Phe | Pro | Pro | Lys | Pro | Lys | Asp | Thr | Leu | Met | Ile | Ser | Arg | Thr | Pro |
| 145 | | | | | 150 | | | | | 155 | | | | | 160 |

| Glu | Val | Thr | Cys | Val | Val | Val | Asp | Val | Ser | His | Glu | Asp | Pro | Glu | Val |
| | | | | 165 | | | | | 170 | | | | | 175 | |

| Lys | Phe | Asn | Trp | Tyr | Val | Asp | Gly | Val | Glu | Val | His | Asn | Ala | Lys | Thr |
| | | | 180 | | | | | 185 | | | | | 190 | | |

| Lys | Pro | Arg | Glu | Glu | Gln | Tyr | Asn | Ser | Thr | Tyr | Arg | Val | Val | Ser | Val |
| | | 195 | | | | | 200 | | | | | 205 | | | |

| Leu | Thr | Val | Leu | His | Gln | Asp | Trp | Leu | Asn | Gly | Lys | Glu | Tyr | Lys | Cys |
| | 210 | | | | | 215 | | | | | 220 | | | | |

| Lys | Val | Ser | Asn | Lys | Ala | Leu | Pro | Ala | Pro | Ile | Glu | Lys | Thr | Ile | Ser |
| 225 | | | | | 230 | | | | | 235 | | | | | 240 |

| Lys | Ala | Lys | Gly | Gln | Pro | Arg | Glu | Pro | Gln | Val | Tyr | Thr | Leu | Pro | Pro |
| | | | | 245 | | | | | 250 | | | | | 255 | |

| Ser | Arg | Asp | Glu | Leu | Thr | Lys | Asn | Gln | Val | Ser | Leu | Thr | Cys | Leu | Val |
| | | | 260 | | | | | 265 | | | | | 270 | | |

| Lys | Gly | Phe | Tyr | Pro | Ser | Asp | Ile | Ala | Val | Glu | Trp | Glu | Ser | Asn | Gly |
| | | | 275 | | | | | 280 | | | | | 285 | | |

| Gln | Pro | Glu | Asn | Asn | Tyr | Lys | Thr | Thr | Pro | Pro | Val | Leu | Asp | Ser | Asp |
| | 290 | | | | | 295 | | | | | 300 | | | | |

| Gly | Ser | Phe | Phe | Leu | Tyr | Ser | Lys | Leu | Thr | Val | Asp | Lys | Ser | Arg | Trp |
| 305 | | | | | 310 | | | | | 315 | | | | | 320 |

| Gln | Gln | Gly | Asn | Val | Phe | Ser | Cys | Ser | Val | Met | His | Glu | Ala | Leu | His |
| | | | | 325 | | | | | 330 | | | | | 335 | |

| Asn | His | Tyr | Thr | Gln | Lys | Ser | Leu | Ser | Leu | Ser | Pro | Gly | Lys |
| | | | 340 | | | | | 345 | | | | | 350 |

<210> SEQ ID NO 38
<211> LENGTH: 350
<212> TYPE: PRT
<213> ORGANISM: Artificial Sequence
<220> FEATURE:
<223> OTHER INFORMATION: SS002M130

<400> SEQUENCE: 38

| | | | | | | | | | | | | | | |
|---|---|---|---|---|---|---|---|---|---|---|---|---|---|---|
|Glu|Leu|Gln|Val|Ile|Gln|Pro|Asp|Lys|Ser|Val|Leu|Val|Ala|Ala|Gly|
|1| | | |5| | | | |10| | | | |15| |
|Glu|Thr|Ala|Thr|Leu|Arg|Cys|Thr|Ala|Thr|Ser|Leu|Leu|Pro|Ile|Gly|
| | | |20| | | | |25| | | | |30| | |
|Pro|Ile|Gln|Trp|Phe|Arg|Gly|Ala|Gly|Pro|Gly|Arg|Val|Leu|Ile|Tyr|
| | |35| | | | |40| | | | |45| | | |
|Asn|Gln|Arg|Glu|Gly|His|Phe|Pro|Arg|Val|Thr|Thr|Val|Ser|Glu|Ser|
| |50| | | | |55| | | | |60| | | | |
|Thr|Arg|Arg|Asp|Asn|Met|Asp|Phe|Ser|Ile|Arg|Ile|Arg|Asn|Ile|Thr|
|65| | | | |70| | | | |75| | | | |80|
|Pro|Ala|Asp|Ala|Gly|Thr|Tyr|Tyr|Cys|Val|Lys|Phe|Arg|Lys|Gly|Ser|
| | | | |85| | | | |90| | | | |95| |
|Pro|Asp|Asp|Val|Glu|Phe|Lys|Ser|Gly|Ala|Gly|Thr|Glu|Leu|Ser|Val|
| | | |100| | | | |105| | | | |110| | |
|Arg|Ala|Lys|Pro|Ser|Leu|Glu|Pro|Lys|Ser|Cys|Asp|Lys|Thr|His|Thr|
| | |115| | | | |120| | | | |125| | | |
|Cys|Pro|Pro|Cys|Pro|Ala|Pro|Glu|Leu|Leu|Gly|Gly|Pro|Ser|Val|Phe|
| |130| | | | |135| | | | |140| | | | |
|Leu|Phe|Pro|Pro|Lys|Pro|Lys|Asp|Thr|Leu|Met|Ile|Ser|Arg|Thr|Pro|
|145| | | | |150| | | | |155| | | | |160|
|Glu|Val|Thr|Cys|Val|Val|Val|Asp|Val|Ser|His|Glu|Asp|Pro|Glu|Val|
| | | | |165| | | | |170| | | | |175| |
|Lys|Phe|Asn|Trp|Tyr|Val|Asp|Gly|Val|Glu|Val|His|Asn|Ala|Lys|Thr|
| | | |180| | | | |185| | | | |190| | |
|Lys|Pro|Arg|Glu|Glu|Gln|Tyr|Asn|Ser|Thr|Tyr|Arg|Val|Val|Ser|Val|
| | |195| | | | |200| | | | |205| | | |
|Leu|Thr|Val|Leu|His|Gln|Asp|Trp|Leu|Asn|Gly|Lys|Glu|Tyr|Lys|Cys|
| |210| | | | |215| | | | |220| | | | |
|Lys|Val|Ser|Asn|Lys|Ala|Leu|Pro|Ala|Pro|Ile|Glu|Lys|Thr|Ile|Ser|
|225| | | | |230| | | | |235| | | | |240|
|Lys|Ala|Lys|Gly|Gln|Pro|Arg|Glu|Pro|Gln|Val|Tyr|Thr|Leu|Pro|Pro|
| | | | |245| | | | |250| | | | |255| |
|Ser|Arg|Asp|Glu|Leu|Thr|Lys|Asn|Gln|Val|Ser|Leu|Thr|Cys|Leu|Val|
| | | |260| | | | |265| | | | |270| | |
|Lys|Gly|Phe|Tyr|Pro|Ser|Asp|Ile|Ala|Val|Glu|Trp|Glu|Ser|Asn|Gly|
| | |275| | | | |280| | | | |285| | | |
|Gln|Pro|Glu|Asn|Asn|Tyr|Lys|Thr|Thr|Pro|Pro|Val|Leu|Asp|Ser|Asp|
| |290| | | | |295| | | | |300| | | | |
|Gly|Ser|Phe|Phe|Leu|Tyr|Ser|Lys|Leu|Thr|Val|Asp|Lys|Ser|Arg|Trp|
|305| | | | |310| | | | |315| | | | |320|
|Gln|Gln|Gly|Asn|Val|Phe|Ser|Cys|Ser|Val|Met|His|Glu|Ala|Leu|His|
| | | | |325| | | | |330| | | | |335| |
|Asn|His|Tyr|Thr|Gln|Lys|Ser|Leu|Ser|Leu|Ser|Pro|Gly|Lys| | |
| | | |340| | | | |345| | | | |350| | |

<210> SEQ ID NO 39
<211> LENGTH: 350
<212> TYPE: PRT
<213> ORGANISM: Artificial Sequence
<220> FEATURE:
<223> OTHER INFORMATION: SS002M135

<400> SEQUENCE: 39

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Leu Leu Ile Tyr
        35                  40                  45

Asn Gly Lys Gly Gly His Phe Pro Arg Val Thr Thr Leu Ser Glu Thr
    50                  55                  60

Thr Arg Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```

<210> SEQ ID NO 40
<211> LENGTH: 350
<212> TYPE: PRT
<213> ORGANISM: Artificial Sequence
<220> FEATURE:
<223> OTHER INFORMATION: SS002M145

<400> SEQUENCE: 40

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Asn Leu Ile Tyr
        35                  40                  45

Asn Gly Lys Gly Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```

<210> SEQ ID NO 41
<211> LENGTH: 346
<212> TYPE: PRT
<213> ORGANISM: Artificial Sequence
<220> FEATURE:
<223> OTHER INFORMATION: SS002M1G4

```
<400> SEQUENCE: 41

Glu Leu Gln Val Ile Gln Pro Asp Lys Ser Val Leu Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Ile Leu Ile Tyr
            35                  40                  45

Asn Gln Lys Lys Gly His Phe Pro Arg Val Thr Leu Ser Asp Ser
        50                  55                  60

Thr Arg Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
            115                 120                 125

Pro Ala Pro Glu Phe Leu Gly Gly Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 42
<211> LENGTH: 346
<212> TYPE: PRT
<213> ORGANISM: Artificial Sequence
<220> FEATURE:
<223> OTHER INFORMATION: SS002M5G4
```

```
<400> SEQUENCE: 42

Glu Leu Gln Val Ile Gln Pro Asp Lys Ser Val Leu Val Ala Ala Gly
1               5                  10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Asn Leu Ile Tyr
        35                  40                  45

Asn Ser Arg His Gly His Phe Pro Arg Val Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 43
<211> LENGTH: 346
<212> TYPE: PRT
<213> ORGANISM: Artificial Sequence
<220> FEATURE:
<223> OTHER INFORMATION: SS002M12G4
```

<400> SEQUENCE: 43

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Ile Gly
                20                  25                  30

Pro Ile Gln Trp Phe Arg Gly Ala Gly Pro Gly Arg Glu Leu Ile Tyr
            35                  40                  45

Asn Gln Arg Lys Gly His Phe Pro Arg Val Thr Thr Val Ser Asp Leu
        50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 44
<211> LENGTH: 346
<212> TYPE: PRT
<213> ORGANISM: Artificial Sequence
<220> FEATURE:
<223> OTHER INFORMATION: SS002M35G4

<400> SEQUENCE: 44

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Val Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 45
<211> LENGTH: 346
<212> TYPE: PRT
<213> ORGANISM: Artificial Sequence
<220> FEATURE:
<223> OTHER INFORMATION: SS002M37G4

<400> SEQUENCE: 45

| Glu | Leu | Gln | Val | Ile | Gln | Pro | Asp | Lys | Ser | Val | Leu | Val | Ala | Ala | Gly |
|---|---|---|---|---|---|---|---|---|---|---|---|---|---|---|---|
| 1 | | | | 5 | | | | | 10 | | | | | 15 | |

| Glu | Thr | Ala | Thr | Leu | Arg | Cys | Thr | Ala | Thr | Ser | Leu | Leu | Pro | Ile | Gly |
| | | | 20 | | | | | 25 | | | | | 30 | | |

| Pro | Ile | Gln | Trp | Phe | Arg | Gly | Ala | Gly | Pro | Gly | Arg | Lys | Leu | Ile | Tyr |
| | | | 35 | | | | | 40 | | | | | 45 | | |

| Asn | Gln | Arg | Asp | Gly | His | Phe | Pro | Arg | Val | Thr | Thr | Val | Ser | Asp | Leu |
| | 50 | | | | | 55 | | | | | 60 | | | | |

| Thr | Lys | Arg | Gly | Asn | Met | Asp | Phe | Ser | Ile | Arg | Ile | Gly | Asn | Ile | Thr |
| 65 | | | | | 70 | | | | | 75 | | | | | 80 |

| Pro | Ala | Asp | Ala | Gly | Thr | Tyr | Tyr | Cys | Val | Lys | Phe | Arg | Lys | Gly | Ser |
| | | | | 85 | | | | | 90 | | | | | 95 | |

| Pro | Asp | Asp | Val | Glu | Phe | Lys | Ser | Gly | Ala | Gly | Thr | Glu | Leu | Ser | Val |
| | | | | 100 | | | | | 105 | | | | | 110 | |

| Arg | Ala | Lys | Pro | Ser | Glu | Ser | Lys | Tyr | Gly | Pro | Pro | Cys | Pro | Pro | Cys |
| | | | 115 | | | | | 120 | | | | | 125 | | |

| Pro | Ala | Pro | Glu | Phe | Leu | Gly | Gly | Pro | Ser | Val | Phe | Leu | Phe | Pro | Pro |
| | | | 130 | | | | | 135 | | | | | 140 | | |

| Lys | Pro | Lys | Asp | Thr | Leu | Met | Ile | Ser | Arg | Thr | Pro | Glu | Val | Thr | Cys |
| 145 | | | | | 150 | | | | | 155 | | | | | 160 |

| Val | Val | Val | Asp | Val | Ser | Gln | Glu | Asp | Pro | Glu | Val | Gln | Phe | Asn | Trp |
| | | | | 165 | | | | | 170 | | | | | 175 | |

| Tyr | Val | Asp | Gly | Val | Glu | Val | His | Asn | Ala | Lys | Thr | Lys | Pro | Arg | Glu |
| | | | 180 | | | | | 185 | | | | | 190 | | |

| Glu | Gln | Phe | Asn | Ser | Thr | Tyr | Arg | Val | Val | Ser | Val | Leu | Thr | Val | Leu |
| | | | 195 | | | | | 200 | | | | | 205 | | |

| His | Gln | Asp | Trp | Leu | Asn | Gly | Lys | Glu | Tyr | Lys | Cys | Lys | Val | Ser | Asn |
| | | 210 | | | | | 215 | | | | | 220 | | | |

| Lys | Gly | Leu | Pro | Ser | Ser | Ile | Glu | Lys | Thr | Ile | Ser | Lys | Ala | Lys | Gly |
| 225 | | | | | 230 | | | | | 235 | | | | | 240 |

| Gln | Pro | Arg | Glu | Pro | Gln | Val | Tyr | Thr | Leu | Pro | Pro | Ser | Gln | Glu | Glu |
| | | | | 245 | | | | | 250 | | | | | 255 | |

| Met | Thr | Lys | Asn | Gln | Val | Ser | Leu | Thr | Cys | Leu | Val | Lys | Gly | Phe | Tyr |
| | | | 260 | | | | | 265 | | | | | 270 | | |

| Pro | Ser | Asp | Ile | Ala | Val | Glu | Trp | Glu | Ser | Asn | Gly | Gln | Pro | Glu | Asn |
| | | 275 | | | | | 280 | | | | | 285 | | | |

| Asn | Tyr | Lys | Thr | Thr | Pro | Pro | Val | Leu | Asp | Ser | Asp | Gly | Ser | Phe | Phe |
| | 290 | | | | | 295 | | | | | 300 | | | | |

| Leu | Tyr | Ser | Arg | Leu | Thr | Val | Asp | Lys | Ser | Arg | Trp | Gln | Glu | Gly | Asn |
| 305 | | | | | 310 | | | | | 315 | | | | | 320 |

| Val | Phe | Ser | Cys | Ser | Val | Met | His | Glu | Ala | Leu | His | Asn | His | Tyr | Thr |
| | | | | 325 | | | | | 330 | | | | | 335 | |

| Gln | Lys | Ser | Leu | Ser | Leu | Ser | Leu | Gly | Lys |
| | | | 340 | | | | | 345 | |

<210> SEQ ID NO 46
<211> LENGTH: 346
<212> TYPE: PRT
<213> ORGANISM: Artificial Sequence
<220> FEATURE:
<223> OTHER INFORMATION: SS002M41G4

<400> SEQUENCE: 46

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg His Leu Ile Tyr
        35                  40                  45

Asn Arg Arg His Gly His Phe Pro Arg Val Thr Thr Val Ser Asp Leu
    50                  55                  60

Thr Lys Arg Asn Asn Met Asp Phe Ser Ile Ser Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 47
<211> LENGTH: 346
<212> TYPE: PRT
<213> ORGANISM: Artificial Sequence
<220> FEATURE:
<223> OTHER INFORMATION: SS002M57G4

<400> SEQUENCE: 47

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Ile Leu Ile Tyr
        35                  40                  45

Asn Gly Lys Arg Gly His Phe Pro Arg Val Thr Thr Leu Ser Asp Thr
    50                  55                  60

Thr Lys Arg Gly Asn Met Asp Phe Ser Ile Ser Ile Arg Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Arg Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 48
<211> LENGTH: 346
<212> TYPE: PRT
<213> ORGANISM: Artificial Sequence
<220> FEATURE:
<223> OTHER INFORMATION: SS002M67G4

<400> SEQUENCE: 48

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Met Leu Ile Tyr
        35                  40                  45

Asn Gly Arg Asp Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 49
<211> LENGTH: 346
<212> TYPE: PRT
<213> ORGANISM: Artificial Sequence
<220> FEATURE:
<223> OTHER INFORMATION: SS002M81G4

<400> SEQUENCE: 49

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 50
<211> LENGTH: 346
<212> TYPE: PRT
<213> ORGANISM: Artificial Sequence
<220> FEATURE:
<223> OTHER INFORMATION: SS002M82G4

<400> SEQUENCE: 50

Glu Leu Gln Val Ile Gln Pro Asp Lys Ser Val Leu Ala Ala Gly
1               5                   10                  15

Glu Thr Ala Thr Leu Arg Cys Thr Ala Thr Ser Leu Phe Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser His Ser
    50                  55                  60

Thr Lys Arg Asn Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 51
<211> LENGTH: 346
<212> TYPE: PRT
<213> ORGANISM: Artificial Sequence
<220> FEATURE:
<223> OTHER INFORMATION: SS002M84G4

<400> SEQUENCE: 51

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Phe Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Val Ser His Ser
    50                  55                  60

Thr Arg Arg Asn Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ser Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 52
<211> LENGTH: 346
<212> TYPE: PRT
<213> ORGANISM: Artificial Sequence
<220> FEATURE:
<223> OTHER INFORMATION: SS002M91G4

<400> SEQUENCE: 52

```
Glu Leu Gln Val Ile Gln Pro Asp Lys Ser Val Leu Val Ala Ala Gly
1               5                   10                  15
Glu Thr Ala Thr Leu Arg Cys Thr Ala Thr Ser Leu Leu Pro Val Gly
            20                  25                  30
Pro Ile Gln Trp Phe Arg Gly Ala Gly Pro Gly Arg Gln Leu Ile Tyr
        35                  40                  45
Asn Gln Lys Asp Gly His Phe Pro Arg Val Thr Thr Ala Ser Asp Leu
    50                  55                  60
Thr Lys Arg Asn Asn Met Asp Phe Ser Ile Asn Ile Gly Asn Ile Thr
65                  70                  75                  80
Pro Ala Asp Ala Gly Thr Tyr Tyr Cys Val Lys Phe Arg Lys Gly Ser
                85                  90                  95
Pro Asp Asp Ile Glu Phe Lys Ser Gly Ala Gly Thr Glu Leu Ser Val
            100                 105                 110
Arg Ala Lys Pro Ser Glu Ser Lys Tyr Gly Pro Pro Cys Pro Pro Cys
        115                 120                 125
Pro Ala Pro Glu Phe Leu Gly Gly Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser Gln Glu Asp Pro Glu Val Gln Phe Asn Trp
                165                 170                 175
Tyr Val Asp Gly Val Glu Val His Asn Ala Lys Thr Lys Pro Arg Glu
            180                 185                 190
Glu Gln Phe Asn Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Gly Leu Pro Ser Ser Ile Glu Lys Thr Ile Ser Lys Ala Lys Gly
225                 230                 235                 240
Gln Pro Arg Glu Pro Gln Val Tyr Thr Leu Pro Pro Ser Gln Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Arg Leu Thr Val Asp Lys Ser Arg Trp Gln Glu Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Leu Gly Lys
            340                 345
```

<210> SEQ ID NO 53
<211> LENGTH: 346
<212> TYPE: PRT
<213> ORGANISM: Artificial Sequence
<220> FEATURE:
<223> OTHER INFORMATION: SS002M99G4

<400> SEQUENCE: 53

Glu Leu Gln Val Ile Gln Pro Asp Lys Ser Val Leu Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Lys Leu Ile Tyr
        35                  40                  45

Asn Gln Lys Glu Gly His Phe Pro Arg Val Thr Thr Val Ser Asp Ser
    50                  55                  60

Thr Lys Arg Lys Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 54
<211> LENGTH: 346
<212> TYPE: PRT
<213> ORGANISM: Artificial Sequence
<220> FEATURE:
<223> OTHER INFORMATION: SS002M102G4

<400> SEQUENCE: 54

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Glu Leu Ile Tyr
        35                  40                  45

Asn Gly Lys Gly Gly His Phe Pro Arg Val Thr Val Ser Arg Ser
    50                  55                  60

Thr Lys Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
                100                 105                 110

Arg Ala Lys Pro Ser Glu Ser Lys Tyr Gly Pro Pro Cys Pro Pro Cys
            115                 120                 125

Pro Ala Pro Glu Phe Leu Gly Gly Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
                180                 185                 190

Glu Gln Phe Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 55
<211> LENGTH: 346
<212> TYPE: PRT
<213> ORGANISM: Artificial Sequence
<220> FEATURE:
<223> OTHER INFORMATION: SS002M111G4

<400> SEQUENCE: 55

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Asn Leu Ile Tyr
        35                  40                  45

Asn Ser Arg His Gly His Phe Pro Arg Val Thr Thr Ala Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 56
<211> LENGTH: 346
<212> TYPE: PRT
<213> ORGANISM: Artificial Sequence
<220> FEATURE:
<223> OTHER INFORMATION: SS002M122G4

<400> SEQUENCE: 56

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg Asn Leu Ile Tyr
        35                  40                  45

Asn Ser Arg His Gly His Phe Pro Arg Val Thr Thr Ala Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 57
<211> LENGTH: 346
<212> TYPE: PRT
<213> ORGANISM: Artificial Sequence
<220> FEATURE:
<223> OTHER INFORMATION: SS002M126G4

<400> SEQUENCE: 57

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Ile Gly
            20                  25                  30

Pro Ile Gln Trp Phe Arg Gly Ala Gly Pro Gly Arg Val Leu Ile Tyr
        35                  40                  45

Asn Gln Arg Asp Gly His Phe Pro Arg Val Thr Val Ser Glu Thr
    50                  55                  60

Thr Arg Arg Glu Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345
```

<210> SEQ ID NO 58
<211> LENGTH: 346
<212> TYPE: PRT
<213> ORGANISM: Artificial Sequence
<220> FEATURE:
<223> OTHER INFORMATION: SS002M130G4

<400> SEQUENCE: 58

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Val Leu Ile Tyr
        35                  40                  45

Asn Gln Arg Glu Gly His Phe Pro Arg Val Thr Thr Val Ser Glu Ser
    50                  55                  60

Thr Arg Arg Asp Asn Met Asp Phe Ser Ile Arg Ile Arg Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 59
<211> LENGTH: 346
<212> TYPE: PRT
<213> ORGANISM: Artificial Sequence
<220> FEATURE:
<223> OTHER INFORMATION: SS002M135G4

<400> SEQUENCE: 59

```
Glu Leu Gln Val Ile Gln Pro Asp Lys Ser Val Leu Val Ala Ala Gly
1               5                   10                  15
Glu Thr Ala Thr Leu Arg Cys Thr Ala Thr Ser Leu Val Pro Val Gly
            20                  25                  30
Pro Ile Gln Trp Phe Arg Gly Ala Gly Pro Gly Arg Leu Leu Ile Tyr
        35                  40                  45
Asn Gly Lys Gly Gly His Phe Pro Arg Val Thr Thr Leu Ser Glu Thr
    50                  55                  60
Thr Arg Arg Gly Asn Met Asp Phe Ser Ile Arg Ile Gly Asn Ile Thr
65                  70                  75                  80
Pro Ala Asp Ala Gly Thr Tyr Tyr Cys Val Lys Phe Arg Lys Gly Ser
                85                  90                  95
Pro Asp Asp Val Glu Phe Lys Ser Gly Ala Gly Thr Glu Leu Ser Val
            100                 105                 110
Arg Ala Lys Pro Ser Glu Ser Lys Tyr Gly Pro Pro Cys Pro Pro Cys
        115                 120                 125
Pro Ala Pro Glu Phe Leu Gly Gly Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser Gln Glu Asp Pro Glu Val Gln Phe Asn Trp
                165                 170                 175
Tyr Val Asp Gly Val Glu Val His Asn Ala Lys Thr Lys Pro Arg Glu
            180                 185                 190
Glu Gln Phe Asn Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Gly Leu Pro Ser Ser Ile Glu Lys Thr Ile Ser Lys Ala Lys Gly
225                 230                 235                 240
Gln Pro Arg Glu Pro Gln Val Tyr Thr Leu Pro Pro Ser Gln Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Arg Leu Thr Val Asp Lys Ser Arg Trp Gln Glu Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Leu Gly Lys
            340                 345
```

<210> SEQ ID NO 60
<211> LENGTH: 346
<212> TYPE: PRT
<213> ORGANISM: Artificial Sequence
<220> FEATURE:
<223> OTHER INFORMATION: SS002M145G4

<400> SEQUENCE: 60

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Asn Leu Ile Tyr
        35                  40                  45

Asn Gly Lys Gly Gly His Phe Pro Arg Val Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Glu Ser Lys Tyr Gly Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 61
<211> LENGTH: 350
<212> TYPE: PRT
<213> ORGANISM: Artificial Sequence
<220> FEATURE:
<223> OTHER INFORMATION: SS002

<400> SEQUENCE: 61

```
Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Leu Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```

<210> SEQ ID NO 62
<211> LENGTH: 504
<212> TYPE: PRT
<213> ORGANISM: Artificial Sequence
<220> FEATURE:
<223> OTHER INFORMATION: Human SIRP variant 1

<400> SEQUENCE: 62

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400
```

```
Ala Gln Gly Ser Thr Ser Ser Thr Arg Leu His Pro Glu Lys Asn
            405                 410                 415

Ala Arg Glu Ile Thr Gln Asp Thr Asn Asp Ile Thr Tyr Ala Asp Leu
            420                 425                 430

Asn Leu Pro Lys Gly Lys Pro Ala Pro Gln Ala Ala Glu Pro Asn
            435                 440                 445

Asn His Thr Glu Tyr Ala Ser Ile Gln Thr Ser Pro Gln Pro Ala Ser
            450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 63
<211> LENGTH: 117
<212> TYPE: PRT
<213> ORGANISM: Artificial Sequence
<220> FEATURE:
<223> OTHER INFORMATION: Truncated domain of human SIRP variant 1

<400> SEQUENCE: 63

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 64
<211> LENGTH: 373
<212> TYPE: PRT
<213> ORGANISM: Artificial Sequence
<220> FEATURE:
<223> OTHER INFORMATION: Extracellular domain of human SIRP domain

<400> SEQUENCE: 64

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
    50                  55                  60
```

```
Pro Ile Gln Trp Phe Arg Gly Ala Gly Pro Gly Arg Glu Leu Ile Tyr
 65                  70                  75                  80

Asn Gln Lys Glu Gly His Phe Pro Arg Val Thr Thr Val Ser Asp Leu
                 85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
        370

<210> SEQ ID NO 65
<211> LENGTH: 108
<212> TYPE: PRT
<213> ORGANISM: Artificial Sequence
<220> FEATURE:
<223> OTHER INFORMATION: IgV domain

<400> SEQUENCE: 65

Gln Pro Asp Lys Ser Val Leu Val Ala Ala Gly Glu Thr Ala Thr Leu
  1               5                  10                  15

Arg Cys Thr Ala Thr Ser Leu Ile Pro Val Gly Pro Ile Gln Trp Phe
                 20                  25                  30

Arg Gly Ala Gly Pro Gly Arg Glu Leu Ile Tyr Asn Gln Lys Glu Gly
             35                  40                  45
```

His Phe Pro Arg Val Thr Thr Val Ser Asp Leu Thr Lys Arg Asn Asn
 50                  55                  60

Met Asp Phe Ser Ile Arg Ile Gly Asn Ile Thr Pro Ala Asp Ala Gly
 65                  70                  75                  80

Thr Tyr Tyr Cys Val Lys Phe Arg Lys Gly Ser Pro Asp Asp Val Glu
                 85                  90                  95

Phe Lys Ser Gly Ala Gly Thr Glu Leu Ser Val Arg
                100                 105

<210> SEQ ID NO 66
<211> LENGTH: 293
<212> TYPE: PRT
<213> ORGANISM: Artificial Sequence
<220> FEATURE:
<223> OTHER INFORMATION: Human CD47

<400> SEQUENCE: 66

Met Trp Pro Leu Val Ala Ala Leu Leu Leu Gly Ser Ala Cys Cys Gly
 1               5                  10                  15

Ser Ala Gln Leu Leu Phe Asn Lys Thr Lys Ser Val Glu Phe Thr Phe
                 20                  25                  30

Cys Asn Asp Thr Val Val Ile Pro Cys Phe Val Thr Asn Met Glu Ala
                 35                  40                  45

Gln Asn Thr Thr Glu Val Tyr Val Lys Trp Lys Phe Lys Gly Arg Asp
 50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
                115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Glu
                290

<210> SEQ ID NO 67
<211> LENGTH: 233
<212> TYPE: PRT
<213> ORGANISM: Artificial Sequence
<220> FEATURE:
<223> OTHER INFORMATION: IgG1-FC

<400> SEQUENCE: 67

Leu Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 68
<211> LENGTH: 229
<212> TYPE: PRT
<213> ORGANISM: Artificial Sequence
<220> FEATURE:
<223> OTHER INFORMATION: IgG4-FC

<400> SEQUENCE: 68

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

```
Glu Val His Asn Ala Lys Thr Lys Pro Arg Glu Gln Phe Asn Ser
65              70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145             150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

FUSION PROTEIN BINDING TO CD47 PROTEIN AND APPLICATION THEREOF

CROSS-REFERENCE TO RELATED APPLICATIONS

This application is a National Stage Application and claims priority under 35 U.S.C. § 371 to Patent Cooperation Treaty application PCT/CN2019/082863, filed Apr. 16, 2019, which claims the benefit of CN 201810343482.9, filed Apr. 17, 2018. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "262790-475658_Seq_Listing_2020-10-14_ST25.txt" is 164,655 bytes in size and was created on Oct. 14, 2020, and filed electronically herewith.

TECHNICAL FIELD

The present application relates to a fusion protein binding to a CD47 protein and use thereof. Said fusion protein can specifically block the interaction between the CD47 protein and SIRPα without causing a blood clotting reaction, and can inhibit the growth and/or proliferation of tumors or tumor cells.

BACKGROUND

CD47 protein is a transmembrane glycoprotein, which is a member of the immunoglobulin superfamily, and expressed on the surface of various cells including red blood cells. Ligands of CD47 comprise intergrins, thrombospondin-1 and signal-regulating proteins (SIRPs). CD47 affects a variety of biological functions, including cell migration, T cells, dendritic cell activation, axon development, etc. Besides, by the interaction with SIRPα, CD47 can inhibit the phagocytosis by macrophages; and protect normal cells, such as, blood cells and the like from being phagocytosed by macrophages. Studies have found that in addition to the expression of CD47 by normal tissue cells, many tumor cells overexpress CD47 and prevent macrophages from phagocytosing the tumor cells by combining with the SIRPα on the surface of macrophages. It is regarded as a mechanism by which tumors evade the body's immune surveillance. Blocking the interaction between the CD47 protein and SIRPα can inhibit growth of tumors (Theocharides APA, et al., 2012).

However, the current reagents for blocking the interaction between the CD47 protein and SIRPα have a limited recognition activity. It tends to have an insufficient affinity with the CD47 protein, and have a limited capacity in inhibiting tumors. In another aspect, the current antibody drugs targeting CD47 have side effects that cause anemia or thrombocytopenia (Yinpeng Bai et al., Chin J Clin Oncol., 2017 Vol 44. No. 7). There is an urgent need for developing a novel therapy that can effectively block the interaction between the CD47 protein and SIRPα with fewer side effects.

SUMMARY OF THE INVENTION

The present application provides a fusion protein binding to a CD47 protein and use thereof. The fusion protein can specifically bind to the CD47 protein. The fusion protein of the present application has at least one of the following characteristics: 1) specifically binding to the CD47 protein with a relatively high affinity; 2) specifically blocking the interaction between the CD47 protein with SIRPα; 3) not causing a blood clotting reaction; 4) inhibiting the growth and/or proliferation of tumors or tumor cells; 5) blocking an apoptotic signal induced by the CD47/SIRPα interaction; and/or 6) being safe for the subject and having no side effects that harm the body. The present application further provides a preparation method and use of the fusion protein.

In one aspect, the present application provides a fusion protein capable of specifically binding to the CD47 protein, and has at least one of the following characteristics: 1) binding to the CD47 protein with a $K_D$ value of $1 \times 10^{-8}$ M or lower; 2) specifically blocking the interaction between the CD47 protein with SIRPα; 3) not causing a blood clotting reaction; and 4) inhibiting the growth and/or proliferation of tumors or tumor cells.

In some embodiments, said CD47 protein is a human CD47 protein.

In some embodiments, said CD47 protein is a CD47 protein expressed on the surface of cells.

In some embodiments, said tumors or tumor cells are CD47-positive.

In some embodiments, said tumors are selected from the group consisting of CD47-positive hematologic tumors and/or CD47-positive solid tumors.

In some embodiments, said fusion protein comprises a human SIRPα domain which can specifically bind to said CD47 protein and an immunoglobulin Fc region, wherein said human SIRPα domain is directly or indirectly linked to the immunoglobulin Fc region.

In some embodiments, said human SIRPα domain comprises an extracellular domain of the human SIRPα, its fragment, or its variant which undergoes one or more amino acid substitutions. In some embodiments, said human SIRPα domain comprises an IgV domain of the human SIRPα, its fragment, or its variant which undergoes one or more amino acid substitutions. In some embodiments, said human SIRPα domain comprises a domain of the human SIRPα variant 1, its fragment, or its variant which undergoes one or more amino acid substitutions. In some embodiments, said human SIRPα domain comprises an IgV domain of the human SIRPα variant 1, its fragment, or its variant which undergoes one or more amino acid substitutions. In some embodiments, said human SIRPα domain comprises amino acid residues at positions 33-149 of the human SIRPα variant 1, its fragment, or its variant which undergoes one or more amino acid substitutions.

In some embodiments, the human SIRPα domain of the present application comprises an amino acid sequence as set forth in any one of SEQ ID NO: 1-20, 62-65, and an amino acid sequence having at least 80% (e.g., at least 85%, at least 90%, at least 91%, at least 92%, at least 93%, at least 94%, at least 95%, at least 96%, at least 97%, at least 98%, at least 99%, or at least 100%) sequence homology thereto.

In some embodiments, the fusion protein of the present application comprises an amino acid sequence as set forth in any one of SEQ ID NO: 21-61, and an amino acid sequence having at least 80% (e.g., at least 85%, at least 90%, at least 91%, at least 92%, at least 93%, at least 94%, at least 95%, at least 96%, at least 97%, at least 98%, at least 99%, or at least 100%) sequence homology thereto.

In some embodiments, said human SIRPα domain, its fragment, or its variant which undergoes one or more amino acid substitutions comprises substitutions, deletions or additions of one or more amino acid residues.

In some embodiments, said mutant comprises amino acid substitutions at one or more residues selected from the group consisting of I61, V63, E77, Q82, K83, E84, V93, D95, D96, K98, N100, R107, G109 and V132.

In some embodiments, said mutant comprises one or more amino acid substitutions selected from the group consisting of R22C, I29L, I61L/V/F, V63I, E77I/N/Q/K/H/M/R/N/V/L, Q82S/R/G/N, K83R, E84K/H/D/R/G, V93L/A, D95H/R/E, D96S/T, K98R, N100G/K/D/E, R107N/S, G109R/H and V132L/R/I/S.

In some embodiments, said human SIRPα domain comprises an amino acid sequence as set forth in any one of SEQ ID NO: 1-20, 62-65.

In some embodiments, said immunoglobulin Fc region comprises an Fc region of IgG.

In some embodiments, said IgG is a human IgG. In some embodiments, said IgG is selected from the group consisting of IgG1 and/or IgG4.

In some embodiments, said human SIRPα domain is located at N-terminus of said immunoglobulin Fc region.

In some embodiments, said human SIRPα domain is linked to the immunoglobulin Fc region via a linker.

In some embodiments, said immunoglobulin Fc region comprises an amino acid sequence as set forth in any one of SEQ ID NO: 67-68.

In some embodiments, said fusion protein comprises an amino acid sequence as set forth in any one of SEQ ID NOS: 21-61.

In another aspect, the present application provides a nucleic acid molecule encoding the fusion protein of the present application.

In another aspect, the present application provides a vector comprising the nucleic acid molecule of the present application.

In another aspect, the present application provides a host cell comprising the nucleic acid molecule of the present application or the vector of the present application.

In another aspect, the present application provides a method of preparing the fusion protein of the present application, said method comprising culturing the host cell of the present application under conditions that allow the expression of the fusion protein.

In another aspect, the present application provides a composition, comprising the fusion protein, the nucleic acid molecule, the vector and/or the host cell of the present application, and optionally pharmaceutically acceptable adjuvants.

In another aspect, the present application provides a use of the fusion protein, the nucleic acid molecule, the vector, the host cell and/or the composition of the present application in preparation of a drug and/or kit, wherein said drug and/or kit is for preventing or treating tumors or autoimmune diseases. In some embodiments, the tumors are selected from the group consisting of CD47-positive hematologic tumors or CD47-positive solid tumors. In some embodiments, the autoimmune diseases are selected from the group consisting of Crohn's disease, allergic asthma and rheumatoid arthritis.

In another aspect, the present application provides a method of blocking the interaction between the CD47 protein and SIRPα, said method comprising administering the fusion protein or the composition of the present application.

In another aspect, the present application provides a method of inhibiting the growth and/or proliferation of tumors or tumor cells, said method comprising contacting the fusion protein or the composition of the present application with the tumors or tumor cells. In some embodiments, the contact occurs in vitro.

In another aspect, the present application provides a method of preventing or treating tumors or autoimmune diseases in a subject, said method comprising administering an effective amount of the fusion protein or the composition of the present application to the subject. In some embodiments, the tumors are selected from the group consisting of CD47-positive hematologic tumors or CD47-positive solid tumors. In some embodiments, the autoimmune diseases are selected from the group consisting of Crohn's disease, allergic asthma and rheumatoid arthritis.

Persons skilled in the art can readily recognize other aspects and advantages of the present disclosure from the detailed description below. The detailed description below only shows and describes exemplary embodiments of the present disclosure. As persons skilled in the art will recognize, the content of the present disclosure enables persons skilled in the art to modify the specific embodiments as disclosed without departing the spirit and scope of the invention that the present application relates to. Correspondingly, the drawings and the description in the specification of the present application are only exemplary, rather than restrictive.

BRIEF DESCRIPTION OF THE DRAWINGS

The specific features of the invention involved in the present application are shown in the appended claims. By reference to the exemplary embodiments as detailedly described below and the accompanying drawings, the features and advantages of the invention involved in the present application can be better understood. The brief description of the accompanying drawings is as follows:

DETAILED DESCRIPTION OF THE EMBODIMENTS

Figure 1:
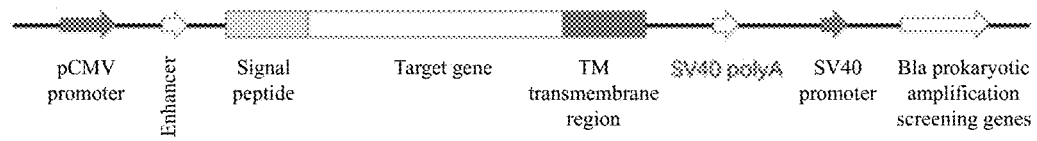
FIG. 1 shows a physical structural schematic view of the vector pTM.

Hereinafter the embodiments of the invention involved in the present application are described by means of specific examples. Persons skilled in the art can readily understand other advantages and effects of the invention involved in the present application through the content disclosed in the present specification.

Fusion Protein

In one aspect, the present application provides a fusion protein which can specifically bind to the CD47 protein with a $K_D$ value of $1 \times 10^{-8}$ M or lower, e.g., a $K_D$ value of no more than $9 \times 10^{-9}$ M, no more than $8 \times 10^{-9}$ M, no more than $7 \times 10^{-9}$ M, no more than $6.2 \times 10^{-9}$ M, no more than $6 \times 10^{-9}$ M, no more than $5 \times 10^{-9}$ M, no more than $4.8 \times 10^{-9}$ M, no more than $4.5 \times 10^{-9}$ M, no more than $2 \times 10^{-9}$ M, no more than $1.5 \times 10^{-10}$ M, or no more than $1 \times 10^{-10}$ M or lower.

In some cases, the fusion protein of the present application can also specifically block the interaction between the CD47 protein and SIRPα, thereby activating macrophages to phagocytose tumor cells, or inhibiting the apoptotic signal of some specific cells. Moreover, the fusion protein of the present application may not cause a blood clotting reaction. For example, said fusion protein and a solution of red blood cells were added into a test hemagglutination plate, and then the red blood cells sunk to the bottom of the well instead of flattening into a mesh. The fusion protein can further inhibit the growth and/or proliferation of tumors or tumor cells, e.g., it can decrease the tumor area or size, or can increase the survival rate of the subject bearing a tumor. The fusion protein is also safe for administration to the subject because it would not negatively affect the body weight and/or death rate of the subject. Moreover, the fusion protein of the present application is easy to prepare and obtain, and not limited to a source of specific immunoglobulin Fc region.

In the present application, the term "fusion protein" generally refers to a complex polypeptide, that is, a single continuous amino acid sequence consisting of two (or more) polypeptides. The fusion protein can generally be artificially prepared by means of recombinant nucleic acid or chemical synthesis.

In the present application, the term "CD47 protein" is also known as integrin associated protein (IAP), which belongs to the immunoglobulin superfamily. The CD47 protein can bind to membrane integrins, thrombospondin-1 (TSP-1) or signal-regulatory protein alpha (SIRPα). The CD47 protein can be expressed on the surface of cell membrane. Said CD47 protein can be a supramolecular complex consisting of specific IAPB, G proteins, and cholesterols. In the present application, said CD47 protein can be a human CD47 protein with the Accession Number being CEJ95640.1 in the GenBank database. In the present application, the CD47 protein can comprise an amino acid sequence shown in SEQ ID NO:66.

In the present application, the term "CD47-positive" generally refers to expression of characteristic of the CD47 protein, its fragment, or its variant which undergoes one or more amino acid substitutions in an organism or the surface of cells. The CD47-positive cells can be cells which overexpress CD47. The CD47-positive cell can generally serve as an indicative of diseases. For example, in the case of diseases, said density of CD47 protein on the surface of the CD47-positive cells will exceed the density of CD47 protein of the same type of cells under normal conditions. In some embodiments, said tumors or tumor cells can be CD47-positive. For example, said tumors can be selected from the group consisting of CD47-positive hematologic tumors and/or CD47-positive solid tumors.

In the present application, the term "$K_D$" can be interchangeably used with "$K_D$", and generally refers to the dissociation constant of a specific antibody-antigen interaction at a unit of M (mol/L). $K_D$ can be calculated by the concentrations of the material AB and the dissociated materials A and B: $K_D = c(A)*c(B)/c(AB)$. It can be seen from the formula that the greater the $K_D$ value, the more the dissociation, and the weaker the affinity of materials A and B; otherwise, the lower the $K_D$ value, the less the dissociation, and the stronger the affinity of materials A and B.

In the present application, the term "SIRPα" generally refers to a regulatory membrane glycoprotein from the SIRP family. Said SIRPα can recognize the CD47 protein, and can serve as the ligand of the CD47 protein. SIRPα is a transmembrane protein, which can have 3 immunoglobulin superfamily-like regions in the extracellular region thereof, wherein the region at the N-terminus mediates the binding to CD47. Said SIRPα is primarily expressed on the surfaces of macrophages, dendritic cells and nerve cells. Said cytoplasmic region of SIRPα is highly conserved in rats, mice, and human. Said SIRPα exhibits a polymorphism which does not however affect its recognition and binding for the CD47 protein.

In the present application, the term "human SIRPα domain" generally comprises a human SIRPα, its fragment, or its variant which undergoes one or more amino acid substitutions. In the present application, said human SIRPα domain can comprise an extracellular domain of the human SIRPα, its fragment, or its variant which undergoes one or more amino acid substitutions. Said human SIRPα domain can comprise an IgV domain of the human SIRPα, its fragment, or its variant which undergoes one or more amino acid substitutions. Said human SIRPα domain can comprise a domain of the human SIRPα variant 1, its fragment, or its variant which undergoes one or more amino acid substitutions. Said human SIRPα domain can comprise amino acid residues at positions 33-149 of the human SIRPα variant 1, its fragment, or its variant which undergoes one or more amino acid substitutions. In human, the SIRPα protein primarily has two types, one type (human SIRPα variant 1 or Type V1) has an amino acid sequence with the GenBank Accession Number of NP 542970.1 (the amino acid sequence thereof is as set forth in SEQ ID NO: 62, wherein the amino acid residues at positions 31-504 can constitute a mature SIRPα domain). The other type (Variant 2 or Type V2) has 13 amino acids different from those in the variant 1 or Type V1, and the amino acid sequence thereof has the GenBank Accession Number of CAA71403.1.

In the present application, said human SIRPα domain can comprise an extracellular domain of the human SIRPα, its fragment, or its variant which undergoes one or more amino acid substitutions.

In the present application, the term "extracellular domain" generally refers to a functional structural region of the protein located outside the cell membrane. In some embodiments, said extracellular domain can refer to the extracellular domain of the human SIRPα domain, its fragment, or its variant which undergoes one or more amino acid substitutions. For example, said extracellular domain of the human SIRPα domain can comprise 3 immunoglobulin superfamily (IgSF) domains and a plurality of glycosylation sites. Said extracellular domain of the human SIRPα domain can bind to a specific ligand (e.g., the CD47 protein), achieving a signal transduction function. Said extracellular domain of the human SIRPα domain can also be activated by a variety of mitogens and be phosphorylated, such as, serum, insulin, growth factors, EGF, PDGF and neurotrophic factors.

In the present application, said human SIRPα domain can comprise an IgV domain of the human SIRPα, its fragment, or its variant which undergoes one or more amino acid substitutions. In the present application, said human SIRPα domain can comprise human SIRPα variant 1, its fragment, or its variant which undergoes one or more amino acid substitutions. For example, said human SIRPα domain can comprise amino acid residues at positions 33-149 of the human SIRPα variant 1, its fragment, or its variant which undergoes one or more amino acid substitutions.

In the present application, the term "IgV domain" generally refers to an IgV-like domain which is similar to the antibody variable domain. The immunoglobulin domain can be divided into four classes: IgV, IgC1, IgC2 and IgI. The IgV domain can be present in different protein families, and comprises the light chain and the heavy chain, the T cell receptor of the immunoglobulin. The human SIRPα can present a high polymorphism in the IgV domain. For example, said IgV domain of the human SIRPα variant 1 can mediate the binding of the human SIRPα domain to the human CD47 protein (Seiffert, M. et al. (2001) Blood 97, 2741-9; Vernon-ffilson, E. F. et al. (2000) Eur J Immunol 30, 2130-7).

For example, said human SIRPα variant 1, its fragment, or its variant which undergoes one or more amino acid substitutions can comprise an amino acid sequence as set forth in SEQ ID NO: 62. For example, said human SIRPα domain can comprise an IgV domain of the human SIRPα variant 1, its fragment, or its variant which undergoes one or more amino acid substitutions. For example, said IgV domain of the human SIRPα variant 1, its fragment, or its variant which undergoes one or more amino acid substitutions can comprise an amino acid sequence as set forth in SEQ ID NO: 65 (i.e., the residues at positions 38-145 of the amino acid sequence as set forth in SEQ ID NO: 62). Alternatively, e.g., said human SIRPα domain can comprise the truncated domain of human SIRPα variant 1, its fragment, or its variant which undergoes one or more amino acid substitutions. Said truncated domain of human SIRPα variant 1, its fragment, or its variant which undergoes one or more amino acid substitutions can comprise an amino acid sequence as set forth in SEQ ID NO: 63 (i.e., the residues at positions 33-149 of the amino acid sequence as set forth in SEQ ID NO: 62).

The human SIRPα domain of the present application can comprise an amino acid sequence as set forth in any one selected from the group consisting of SEQ ID NO: 1-20 and 62-65.

In the present application, the term "mutant" generally refers to a protein, polypeptide or amino acid sequence in which a mutation occurs. Said mutation can refer to the difference as compared with the wild type. For example, said mutation can be a structural change of the amino acid sequence which occurs on the basis of the wild type. For example, said wild type can be a typical phenotype lacking said structural change. For example, said mutant can be obtained upon the mutation of the human SIRPα domain, its fragment (comprising an IgV domain of the human SIRPα, its fragment, a domain of the human SIRPα variant 1, its fragment or amino acid residues at positions 33-149 of the human SIRPα variant 1, its fragment) which is deemed as the wild type.

In the present application, the mutant can comprise amino acid substitutions at one or more residues selected from the group consisting of I61, V63, E77, Q82, K83, E84, V93, D95, D96, K98, N100, R107, G109, and V132. Said positions of the amino acid residues of amino acid substitutions can be a precise residue number by using the amino acid sequence as set forth in SEQ ID NO: 62 as reference, wherein the "residue Xn" refers to the residue X corresponding to the position n in the amino acid sequence as set forth in SEQ ID NO: 62, wherein n is a positive integer, X is an abbreviation of any amino acid residue. For example, the "residue I61" refers to the amino residue I corresponding to position 61 in the amino acid sequence as set forth in SEQ ID NO:62.

In the present application, the "amino acid substitution Xn" refers to an amino acid substitution occurring in the amino acid residue X at position n of the amino acid sequence as set forth in SEQ ID NO: 62, wherein n is a positive integer, X is an abbreviation of any amino acid residue. For example, the "amino acid substitutions I61" refers to the amino acid substitution occurring in the amino acid residue I corresponding to position 61 of the amino acid sequence as set forth in SEQ ID NO:62.

In the present application, a certain amino acid residue in a certain amino acid sequence "corresponding to" a certain amino acid residue in another amino acid sequence generally refers to a corresponding relationship of amino acid residue obtained by the alignment of amino acid sequence under optimizing conditions. Said sequence alignment can be carried out by means that persons skilled in the art understand, e.g., by use of BLAST, BLAST-2, ALIGN, NEEDLE or Megalign (DNASTAR) softwares, etc. Persons skilled in the art can determine the appropriate parameters for use in the alignment, comprising any algorithm required to achieve optimal alignment in the full-length sequence being compared.

The amino acid substitutions of the present application can be non-conserved substitutions. Said non-conserved substitutions can comprise changing the amino acid residues in a target protein or polypeptide in a non-conserved manner, e.g., replacing an amino acid residue having a certain side chain size or a certain characteristic (e.g., hydrophilic) with an amino acid residue having a different side chain size or a different characteristic (e.g., hydrophobic).

Said amino acid substitutions can also be conserved substitutions. Said conserved substitutions can comprise changing the amino acid residues in a target protein or polypeptide in a conserved manner, e.g., replacing an amino acid residue having a certain side chain size or a certain characteristic (e.g., hydrophilic) with an amino acid residue having the same or similar side chain size or the same or similar characteristic (e.g., still hydrophilic). Such conserved substitutions generally would not produce a significant effect on the structure or the function of the produced protein. In the present application, the amino acid sequence variant which is a mutant of the fusion protein, its fragment, or its variant which undergoes one or more amino acid substitutions can comprise conserved amino acid substitutions that would not remarkably change the structure or function of the protein (e.g., an ability of blocking the binding of CD47 to its ligand).

As an example, the mutual substitutions between amino acids in each of the following groups can be considered as conservative substitutions in the present application:

Group of amino acids with nonpolar side side(s): alanine, valine, leucine, isoleucine, proline, phenylalanine, tryptophan and methionine.

Group of uncharged amino acids with polar side chains: glycine, serine, threonine, cysteine, tyrosine, asparagine and glutamine.

Group of negatively charged amino acids with polar side chains: aspartic acid and glutamic acid.

Group of positively charged basic amino acids: lysine, arginine and histidine. Group of amino acids with phenyl: phenylalanine, tryptophan and tyrosine.

In some embodiments, said mutant can comprise one or more amino acid substitutions selected from the group consisting of I61L/V/F, V63I, E77I/N/Q/K/H/M/R/N/V/L, Q82S/R/G/N, K83R, E84K/H/D/R/G, V93L/A, D95H/R/E, D96S/T, K98R, N100G/K/D/E, R107N/S, G109R/H and V132L/R/I/S.

In the present application, the amino acid substitutions "XnY/Z" means that the residue X corresponding to position n in the amino acid sequence as set forth in SEQ ID NO: 62 is substituted with an amino acid residue Y or an amino acid residue Z, wherein n is a positive integer, X, Y and Z are independently an abbreviation of any amino acid residue, respectively, and X is different from Y or Z. For example, the amino acid substitution "I61L/V/F" means that the residue I corresponding to position 61 of the amino acid sequence as set forth in SEQ ID NO: 62 is substituted with an amino acid residue L, V or F.

For example, the fusion protein of the present application can comprise an amino acid substitution group selected from the group consisting:

(1) I61L, V63I, E77I, E84K, V93L, L96S, K98R, N100G and V132L;
(2) I61V, E77N, Q82S, K83R and E84H;
(3) I61F, V63I, K83R, E84K and V132I;
(4) I61L, E77Q, E84D, R107N and V132I;
(5) I61L, V63I, E77K, K83R, E84D and N100G;
(6) I61V, E77H, Q82R, K83R, E84H and R107S;
(7) I61L, E77I, Q82G, E84R, V93L, L96T, N100G, R107S, G109R and V132R;
(8) I61L, E77M, Q82G, K83R, E84D and V132L;
(9) I61L;
(10) I61F, D95H, L96S, G109H and V132S;
(11) I61F, D95H, L96S, K98R, G109H and V132S;
(12) I61L, E77Q, E84D, V93A, R107N and V132I;
(13) E77K, L96S, N100K, G109H and V132L;
(14) I61L, V63I, Q82G, E84G, D95R, L96S, N100D and V132I;
(15) I61L, E77R, Q82N, K83R, E84G, V93L, D95E, L96T, K98R, N100D and V132L;
(16) I61V, E77N, Q82S, K83R, E84H and V93A;
(17) I61V, V63I, E77V, K83R, E84D, D95E, L96T, K98R and N100E;
(18) I61L, V63I, E77V, K83R, D95E, L96S, K98R, N100D and G109R;
(19) I61V, E77L, Q82G, E84G, V93L, D95E, L96T, K98R and N100G; and
(20) I61L, V63I, E77N, Q82G and E84G.

In the present application, the variants of the SIRPα domain respectively comprising one group of the amino acid substitutions of the above (1) to (20) on the basis of the truncated domain of human SIRPα variant 1 (the amino acid sequence as set forth in SEQ ID NO: 63, that is, the residues at positions 33-149 of the amino acid sequence as set forth in SEQ ID NO: 62) can be sequentially named M1, M5, M12, M35, M37, M41, M57, M67, M81, M82, M84, M91, M99, M102, M111, M122, M126, M130, M135 and M145. These mutants can sequentially comprise the amino acid sequences shown in one of SEQ ID NO: 1 to SEQ ID NO: 20.

In the present application, the fusion protein comprising the truncated domain of human SIRPα variant 1 (the amino acid sequence as set forth in SEQ ID NO: 63, namely, the residues at positions 33-149 of the amino acid sequence as set forth in SEQ ID NO: 62) and the human IgG1 Fc (the amino acid sequence as set forth in SEQ ID NO: 67) can be sequentially named SS002 that comprises the amino acid sequence as set forth in SEQ ID NO: 61.

In the present application, the term "immunoglobulin Fc region" generally refers to the base region of the Y-shaped structure of the antibody structure, which is also called the fragment crystallizable region (Fc region). In IgG, IgA and IgD antibody isotypes, the Fc region can be composed of two identical protein fragments derived from the second and the third constant domains of the two heavy chains of the antibody. The Fc regions of IgM and IgE can comprise three heavy chain constant domains in each polypeptide chain. The Fc region of IgG has a highly conserved N-glycosylation site. In some embodiments, said immunoglobulin Fc region can comprise the Fc region of IgG. In some embodiments, said immunoglobulin Fc region can include the CH2 and CH3 regions of the heavy chain constant region. In some embodiments, said immunoglobulin Fc region can comprise a hinge region. For example, said immunoglobulin Fc region can comprise an amino acid sequence selected from any one of the following: SEQ ID NO: 67-68.

In the present application, the term "IgG" generally refers to the immunoglobulin G (Immunoglobulin G). IgG is one of the human immunoglobulins. According to the difference of the antigenity of gamma chain in the IgG molecules, the human IgG has four subtypes: IgG1, IgG2, IgG3 and IgG4. In the present application, the term "IgG1" generally refers to one subtype with the highest proportion of IgG that has a relatively high affinity with the Fc receptor. For example, said IgG can be a human IgG. Alternatively, e.g., said IgG can be selected from the group consisting of IgG1 and/or IgG4.

In the present application, said fusion protein comprises a human SIRPα domain which can specifically bind to the CD47 protein and an immunoglobulin Fc region, wherein the human SIRPα domain can be directly or indirectly linked to the immunoglobulin Fc region. For example, said human SIRPα domain can be located at N-terminus of the immunoglobulin Fc region. For example, said C-terminus of the human SIRPα domain can be directly or indirectly linked to the N-terminus of the immunoglobulin Fc. For example, said human SIRPα domain can be linked to said immunoglobulin Fc via a linker. In the present application, said linker can be a peptide linker.

In the present application, the fusion protein of the present application comprising one group of amino acid substitutions of (1)-(20) as above on the basis of said SS002, respectively can be sequentially named SS002M1, SS002M5, SS002M12, SS002M35, SS002M37, SS002M41, SS002M57, SS002M67, SS002M81, SS002M82, SS002M84, SS002M91, SS002M99, SS002M102, SS002M111, SS002M122, SS002M126, SS002M130, SS002M135 and SS002M145. These fusion proteins can sequentially comprise the amino acid sequence as set forth in SEQ ID NO: 21-SEQ ID NO: 40.

In the present application, the fusion protein of the present application respectively comprising one group of amino acid substitutions of the above (1)-(20) and the human IgG4 Fc (the amino acid sequence as set forth in SEQ ID NO: 68) on the basis of the truncated domain of human SIRPα variant 1 (comprising the amino acid sequence of SEQ ID NO: 63, that is, the residues at positions 33-149 in the amino acid sequence as set forth in SEQ ID NO: 62) can be sequentially named SS002M1G4, SS002M5G4, SS002M12G4, SS002M35G4, SS002M37G4, SS002M41G4, SS002M57G4, SS002M67G4, SS002M81G4, SS002M82G4, SS002M84G4, SS002M91G4, SS002M99G4, SS002M102G4, SS002M111G4, SS002M122G4, SS002M126G4, SS002M130G4, SS002M135G4 and SS002M145G4. These fusion proteins can sequentially comprise the amino acid sequence as set forth in one of SEQ ID NO: 41 to SEQ ID NO: 60.

In some embodiments, the fusion protein of the present application can comprise an amino acid sequence as set forth in any one of SEQ ID NO: 21-SEQ ID NO: 61.

The protein, polypeptide and/or amino acid sequence involved in the present application can also be understood to comprise at least the following scope: variants or homologues with the same or similar function as said protein or polypeptide.

In the present application, said variants can be protein or polypeptides generated by the substitution, deletion, or addition of one or more amino acids as compared with the amino acid sequence of said protein and/or said polypeptide (e.g., the human SIRPα domain, its fragment, or its variant which undergoes one or more amino acid substitutions; or said fusion protein). For example, said functional variant can comprise proteins or polypeptides with amino acid changes by the substitution, deletion and/or insertion of at least 1 amino acid, e.g., 1-30, 1-20 or 1-10, alternatively, e.g., 1, 2, 3, 4 or 5 amino acid substitutions, deletions and/or insertions. Said functional variant can substantially retain the biological characteristics of said protein or said polypeptide before change (e.g., substitutions, deletions or additions). For example, said functional variant can retain at least 60%, 70%, 80%, 90%, or 100% of biological activity (e.g., the ability of specifically binding to the CD47 protein) of said protein or said polypeptide before change.

In the present application, said homologue can be a protein or polypeptide which has at least about 80% (e.g., at least about 85%, about 90%, about 91%, about 92%, about 93%, about 94%, about 95%, about 96%, about 97%, about 98%, about 99% or more) sequence homology with the amino acid sequence of said protein and/or said polypeptide (e.g., the human SIRPα domain, its fragment, or its variant which undergoes one or more amino acid substitutions; or said fusion protein).

In the present application, said homology generally refers to the similarity, analogousness or association between two or more sequences. The "percent of sequence homology" can be calculated by ways of comparing the two sequences to be aligned in the comparison window to determine the number of positions at which the same nucleic acid base (e.g., A, T, C, G, I) or the same amino acid residue (e.g., Ala, Pro, Ser, Thr, Gly, Val, Leu, Ile, Phe, Tyr, Trp, Lys, Arg, His, Asp, Glu, Asn, Gln, Cys and Met) are present so as to give the number of matching positions, dividing the number of matching positions by the total number of positions in the comparison window (i.e., the window size), and multiplying the result by 100 to give the percent of the sequence homology. The alignment to determine the percent of the sequence homology can be performed in a variety of ways known in the art, e.g., by use of publicly available computer softwares, such as, BLAST, BLAST-2, ALIGN or Megalign (DNASTAR) softwares. Persons skilled in the art can determine the appropriate parameters for sequence alignment, including any algorithm required to achieve the maximum alignment within the full-length sequence being compared or within the target sequence region. Said homology can also be determined by the following methods: FASTA and BLAST. The FASTA algorithm is described in, e.g., W. R. Pearson and D. J. Lipman's "Improved Tool for Biological Sequence Comparison", Proc. Natl. Acad. Sci., 85: 2444-2448, 1988; and D, J. Lipman and W. R. Pearson's "Fast and Sensitive Protein Similarity Search", Science, 227:1435-1441, 1989. For the description of BLAST algorithm, please refer to S. Altschul, W. Gish, W. Miller, E. W. Myers and D. Lipman, "A Basic Local Alignment Search Tool", Journal of Molecular Biology, 215: 403-410, 1990.

Nucleic Acid Molecule, Vector, Host Cell

In another aspect, the present application provides one or more nucleic acid molecules capable of encoding the fusion protein of the present application.

In some embodiments, said nucleic acid molecule can completely encode the fusion protein of the present application. For example, said fusion protein can be obtained by use of only one type of nucleic acid molecule. In some embodiments, said nucleic acid molecule can encode a part of the fusion protein of the present application. For example, said fusion protein can be obtained by use of more than two types of different said nucleic acid molecules. For example, said nucleic acid molecule can encode said human SIRPα domains of the fusion protein of the present application (e.g., said extracellular domain of the human SIRPα, its fragment, or its variant which undergoes one or more amino acid substitutions, said IgV domain of the human SIRPα, its fragment, or its variant which undergoes one or more amino acid substitutions, said domain of the human SIRPα variant 1, its fragment, or its variant which undergoes one or more amino acid substitutions). Alternatively, e.g., said nucleic acid molecule can encode the immunoglobulin Fc region of the fusion protein.

In another aspect, the present application provides one or more vectors which can comprise one or more nucleic acid molecules of the present application. In another aspect, the present application provides a cell (e.g., a host cell), which can comprise the nucleic acid molecule of the present application or the vector of the present application.

In the present application, the term "nucleic acid molecule" generally refers to an isolated form of nucleotide, deoxyribonucleotide or ribonucleotide or their analogs of any length isolated from their natural environment or artificially synthesized. The nucleic acid molecules of the present application can be isolated. For example, it can be produced or synthesized by the following ways: (i) in vitro amplification, such as polymerase chain reaction (PCR) amplification, (ii) clonal recombination, (iii) purification, e.g., fractionation by restriction enzyme digestion and gel electrophoresis, or (iv) synthesis, e.g., chemical synthesis. In some embodiments, said isolated nucleic acid is a nucleic acid molecule prepared by a recombinant DNA technology. In the present application, the nucleic acid encoding said antibody or its antigen-binding fragment can be prepared by a variety of methods known in the art. These methods include, but are not limited to, overlap extension PCR by use of restriction fragment operations or synthetic oligonucleotides. Specific operations can be found in Sambrook et al., Molecular Cloning, A Laboratory Manual, Cold Spring Harbor Laboratory Press, Cold Spring Harbor, N.Y., 1989; and Ausube et al. Current Protocols in Molecular Biology, Greene Publishing and Wiley-Interscience, New York N.Y., 1993.

In the present application, the term "vector" generally refers to a nucleic acid molecule capable of self-replication in a suitable host, which transfers the inserted nucleic acid molecule into a host cell and/or between host cells. Said vector can comprise a vector mainly used for inserting DNA or RNA into cells, a vector mainly used for replicating DNA or RNA, and a vector mainly used for the transcription of DNA or RNA and/or expression of translation. Said vector also comprises a vector with multiple functions described above. Said vector can be a polynucleotide that can be transcribed and translated into a polypeptide when introduced into a suitable host cell. Generally, by culturing a suitable host cell containing said vector, said vector can produce the desired expression product. In the present application, said vector can include one or more of said nucleic acid molecules. For example, said vector can comprise all the nucleic acid molecules required for encoding said fusion protein. In this case, only one vector is required to obtain the fusion protein of the present application. In some embodiments, said vector can comprise a nucleic acid molecule encoding a part of said fusion protein, e.g., a nucleic acid molecule encoding said human SIRPα domain in the fusion protein of the present application. Alternatively, said vector can comprise, e.g., a nucleic acid molecule encoding said Fc region of the immunoglobulin in said fusion protein. At this time, two or more different vectors are required to obtain the fusion protein of the present application.

In addition, said vector can also include other genes, such as a marker gene that allows selecting the vector in a suitable host cell and under suitable conditions. In addition, said vector can also include an expression control element that allows the coding region to be properly expressed in a suitable host. Such control element is well known to those skilled in the art. For example, they can comprise promoters, ribosome binding sites, enhancers, and other control elements that regulate gene transcription or mRNA translation. In some embodiments, said expression control sequence is a regulatory element. The specific structure of said expression control sequence can vary depending on the function of the species or cell types, but usually comprises 5' non-transcribed sequences and 5' and 3' non-translated sequences involved in transcription and translation initiation, such as TATA boxes, capped sequences, CAAT sequences, etc. For example, the 5' non-transcribed expression control sequence can comprise a promoter region, and the promoter region can comprise a promoter sequence for transcriptional control of the functionally linked nucleic acid. In the present application, said vector can be a pTM vector.

In the present application, the terms "host cell", "cell", and "host" are used interchangeably, and generally refer to a plasmid or vector that can include or have included the nucleic acid molecule of the present application, or can express individual cells, cell lines or cell cultures of the fusion protein of the present application, its fragments or its variants. Said host cell can comprise the progeny of a single host cell. Due to natural, accidental or deliberate mutations, the progeny cells and the original parent cells can not necessarily be completely identical in morphology or genome, as long as they can express the antibodies of the present application or its antigen-binding fragments. Said host cell can be obtained by transfecting cells in vitro with the vector of the present application. Said host cell can be a prokaryotic cell (e.g., *Escherichia coli*) or a eukaryotic cell (e.g., yeast cells, e.g., COS cells, Chinese Hamster Ovary (CHO) cells, HeLa cells, HEK293 cells, COS-1 cells, NS0 cells or myeloma cells). In the present application, said host cell can be a CHO cell.

Composition, Preparation Method and Use

In another aspect, the present application can provide a method of preparing said fusion protein, including culturing a host cell under conditions that allow the expression of said fusion protein.

In another aspect, the present application can provide a composition comprising said fusion protein, said nucleic acid molecule, said vector and/or said host cell, and optionally a pharmaceutically acceptable adjuvant.

In the present application, the term "pharmaceutically acceptable adjuvant" can comprise buffers, antioxidants, preservatives, low molecular weight polypeptides, proteins, hydrophilic polymers, amino acids, sugars, chelating agents, counterions, metal complexes and/or nonionic surfactants, etc.

Said pharmaceutically acceptable adjuvant can comprise buffers, antioxidants, preservatives, low molecular weight polypeptides, proteins, hydrophilic polymers, amino acids, sugars, chelating agents, counter-ions, metal complexes, and/or nonionic surfactants etc.

In the present application, said pharmaceutical composition can be formulated with a pharmaceutically acceptable carrier or diluent and any other known adjuvants and excipients according to conventional technical means in the art, e.g., following the operations in Remington: The Science and Practice of Pharmacy, nineteenth edition, edited by Gennaro, Mack Publishing Co., Easton, Pa., 1995.

In the present application, said composition can be formulated for oral administration, intravenous administration, intramuscular administration, in situ administration at the tumor site, inhalation, rectal administration, vaginal administration, transdermal administration or the medicine is administered via a subcutaneous depot.

In the present application, said composition can be used to inhibit the tumor growth. For example, the composition of the present application can inhibit or delay the development or progression of diseases (e.g., tumors or autoimmune diseases), (e.g., reduce the tumor size or even substantially eliminate the tumors), and/or can reduce and/or stabilize the disease status.

The pharmaceutical composition of the present application can comprise a therapeutically effective amount of said fusion protein. Said therapeutically effective amount is a dose required to prevent and/or treat (at least partially treat)

diseases (e.g., tumors or autoimmune diseases) and/or any complications thereof in a subject with or at a risk of the diseases.

In another aspect, the present application provides use of the fusion protein, the nucleic acid molecule, the vector, the host cell and/or the composition of the present application in the preparation of a drug and/or a kit for use in prevention or treatment of tumors or autoimmune diseases.

In the present application, the term "tumor" usually refers to new growths formed by proliferation of local tissue cells of organisms. Since such new growths are mostly presented as mass-occupying bulges, they are also called neoplasms. According to the cell characteristics of new growths and the degree of harm to the body, tumors are further divided into two classes, that is, benign tumors and malignant tumors. Cancer is the general term for malignant tumors. The tumors of the present application can be selected from the group of CD47-positive hematological tumors and/or CD47-positive solid tumors.

In the present application, the term "CD47-positive hematological tumor" generally refers to hematological tumors that overexpress CD47, which can comprise a variety of leukemias, lymphomas and myelomas. Said "leukemia" generally refers to a cancer of the blood, in which too many white blood cells are produced that are not effective in fighting against infection, thereby squeezing other parts of the blood, such as platelets and red blood cells. Leukemias can be divided into acute or chronic leukemias. Some forms of leukemia can be, e.g., acute lymphocytic leukemia (ALL), acute myeloid leukemia (AML), chronic lymphocytic leukemia (CLL), chronic myelogenous leukemia (CML), myeloproliferative disorder/tumor (MPDS), and myelodysplastic syndrome. Said "lymphoma" may refer to Hodgkin's lymphomas, indolent and aggressive non-Hodgkin's lymphomas, Burkitt's lymphoma, follicular lymphoma (small cell and large cell), etc. Said myelomas can refer to multiple myeloma (MM), giant cell myeloma, heavy chain myeloma (heavy chain myeloma), light chain myeloma (light chain myeloma), or Bence-Jones myeloma (Bence-Jones myeloma).

In the present application, the term "CD47-positive solid tumor" generally refers to a solid tumor or a visible tumor that overexpresses CD47, which can be detected by clinical examination, such as, X-ray film, CT scanning, B-ultrasound or palpation. Major categories can comprise carcinomas and sarcomas. For example, said CD47-positive solid tumors can include Ewing's sarcoma, osteosarcoma, rhabdomyosarcoma, bladder cancer, ovarian cancer, prostate cancer, lung cancer, colon cancer, breast cancer, pancreatic cancer, astrocytic carcinoma, glioblastoma, renal cell carcinoma, etc.

In the present application, said autoimmune diseases can include Crohn's disease, allergic asthma, and rheumatoid arthritis.

In the present application, the term "Crohn's disease" generally refers to an intestinal inflammatory disease of unknown cause, which can occur in any part of the gastrointestinal tract. Both said Crohn's disease and chronic non-specific ulcerative colitis are collectively referred to as inflammatory bowel disease (IBD).

In the present application, the term "allergic asthma" generally refers to chronic airway inflammations involved by a variety of cells, especially mast cells, eosinophils and T lymphocytes.

In the present application, the term "rheumatoid arthritis" generally refers to a chronic systemic autoimmune disease dominated by joint disease.

In another aspect, the fusion protein, the nucleic acid molecule, the vector, the host cell and/or the composition of the present application can be used in preventing or treating said tumors or said autoimmune diseases.

In another aspect, the present application provides a method for preventing or treating tumors or autoimmune diseases, including administering the fusion protein, the nucleic acid molecule, the vector, the host cell and/or the composition of the present application to a subject.

In another aspect, the present application provides a method of blocking the interaction of CD47 protein and the SIRPα, comprising administering the fusion protein or the composition of the present application (e.g., administering to a subject or cell or biological sample in need thereof).

In another aspect, the present application provides a method of inhibiting the growth and/or the proliferation of tumors or tumor cells, comprising contacting the fusion protein or the composition of the present application with the tumors or tumor cells. For example, said contact can occur in vitro.

In the present application, the term "subject" generally refers to any human or non-human animal. The term "non-human animal" can include all vertebrates, such as, mammals and non-mammals, e.g., non-human primates, goats, sheep, dogs, cows, chickens, amphibians, reptiles, etc.

In the present application, the term "about" generally refers to a variation within 0.5%-10% of the specified value, e.g., within 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the specified value.

In the present application, the term "comprising" usually means including, containing, having or encompassing. In some cases, it also refers to the meaning of "being" or "consisting of".

Without being limited by any theory, the following examples are only for the purpose of illustrating the working modes of the apparatus, method and system of the present application, rather than for limiting the scope of the invention as claimed in the present application.

EXAMPLES

Example 1: Screening of Variants

The truncated domain of human SIRPα variant 1 (NP 542970.1) with an amino acid sequence as set forth in SEQ ID NO: 63 (i.e., residues at positions 33-149 in SEQ ID NO: 62) were taken, and Discovery Studio (Neotrident) software was used to construct the structure in the truncated domain that interacted with the human CD47 (CEJ95640.1). The interaction sites in the two proteins and the interaction modes thereof were theoretically analyzed to determine that the amino acid sites in the truncated domains which directly or indirectly participated in the interaction with CD47 were I61, V63, E77, Q82, K83, E84, V93, D95, D96, K98, N100, R107, G109, and V132 (in which the positions of the amino acid residues in the amino acid substitutions were numbered by use of the amino acid sequence set forth in SEQ ID NO: 62 as reference). These action sites were randomly mutated, and a mutant library was constructed. Then, the mutant library was cloned into the vector pTM. Said pTM vector comprised a signal peptide and a transmembrane region sequence (as shown in FIG. 1), which could display the gene cloned into the vector on the cell surface.

Figure 2:
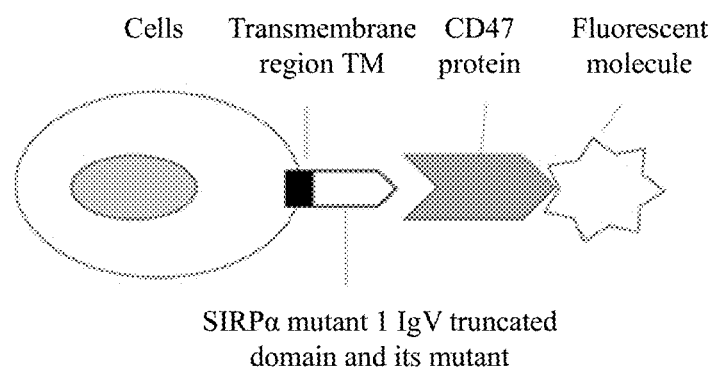
FIG. 2 shows a schematic view of method of detecting the interactions between the SIRPα truncated domains and a mutant thereof and CD47.

The expression vector of the constructed mutant library was transfected into CHO cells (ATCC), so as to display and express the mutant library on the cell surface. Then, a CD47 protein (Yiqiao Shenzhou) was fluorescently labeled with FITC to obtain CD47-FITC. According to the difference of the binding activity between CD47-FITC and the mutants of the truncated domain on the surface of CHO cells, the mutants which bind to CD47-FITC were enriched and screened via flow cytometric technology. The specific screening principle could be seen in FIG. 2, wherein the truncated domain and the mutant binded to the CD47 protein with the fluorescent molecule, therefore, the binding results could be reflected by the level of the fluorescent molecule.

Figure 3:
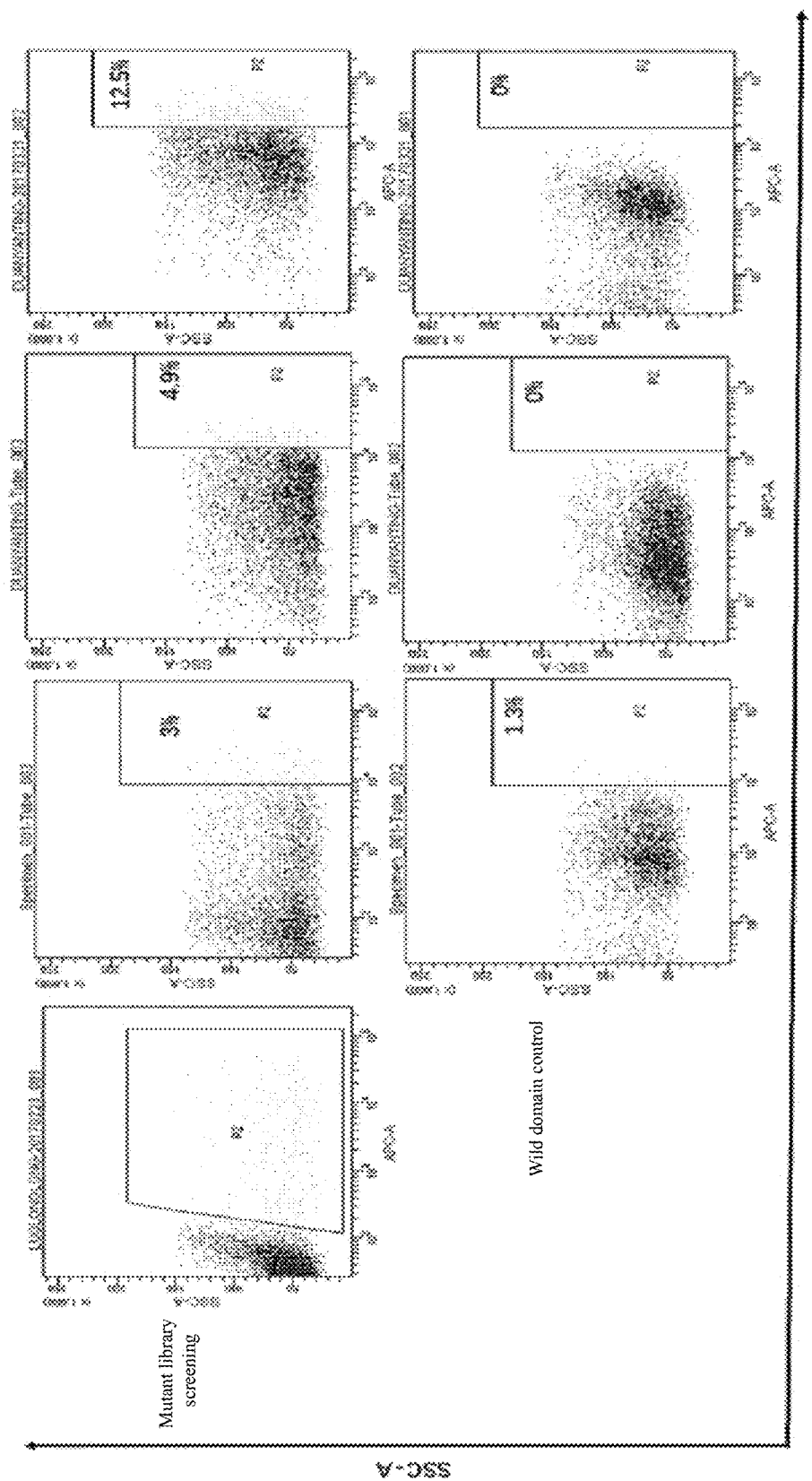
FIG. 3 shows the results of enrichment screening of SIRPα truncated domain mutants by flow cytometry.
Figure 4:
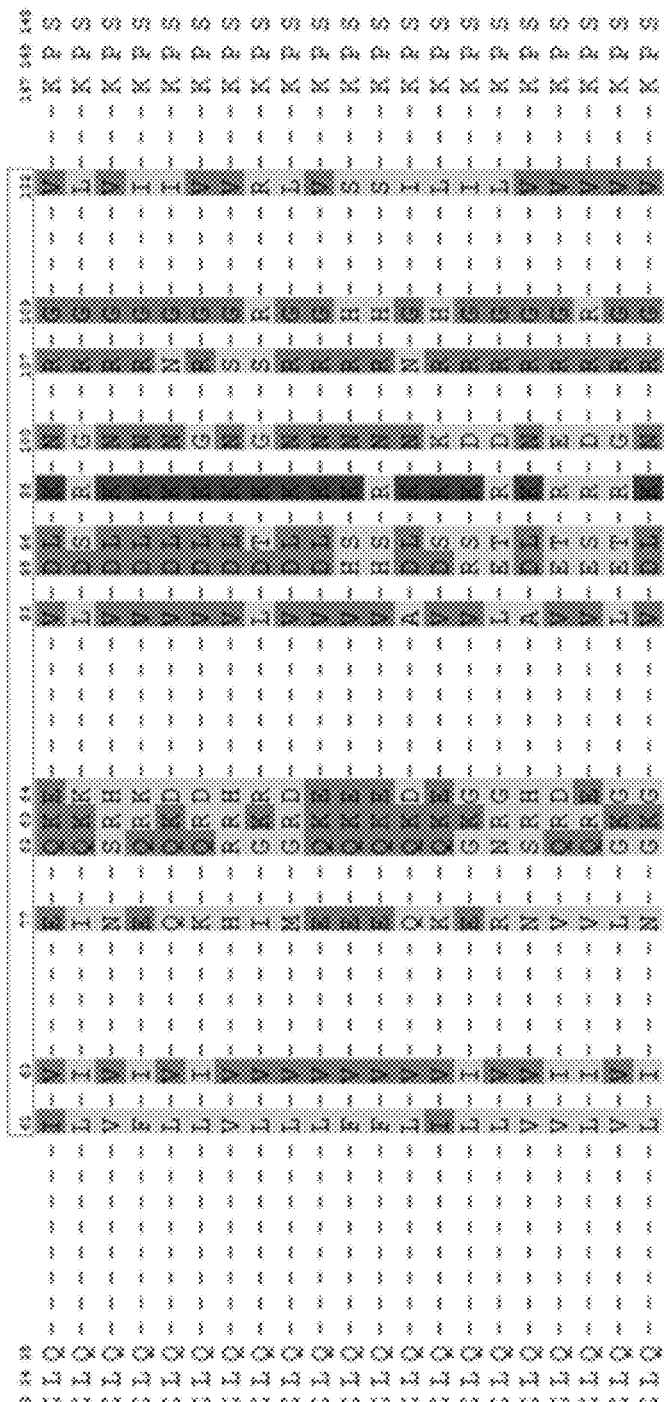
FIG. 4 shows the sequence alignment of SIRPα truncated domains and their variants.

After four rounds of screening and enrichment, cells that bound strongly to CD47-FITC were collected (as shown in FIG. 3). Then, the mRNA was extracted and subject to reverse transcription to give cDNA, and the truncated domain mutant was subject to sequencing analysis (as shown in FIG. 4). The sequencing results showed that the aforesaid positions I61, V63, E77, Q82, K83, E84, V93, D95, D96, K98, N100, R107, G109, V132 have different combinations of mutation sites.

It could be seen from the results that a mutant of the human SIRPα variant 1 truncated domain that can specifically recognize CD47 can be obtained by introducing different combinations of mutation sites at residues I61, V63, E77, Q82, K83, E84, V93, D95, D96, K98, N100, R107, G109, and/or V132.

Further analysis gave the possible types of the mutated amino acids of the aforesaid mutation sites: I61L/V/F, V63I, E77I/N/Q/K/H/M/R/N/V/L, Q82S/R/G/N, K83R, E84K/H/D/R/G, V93L/A, D95H/R/E, D96S/T, K98R, N100G/K/D/E, R107N/S, G109R/H, V132L/R/I/S.

The mutants containing these mutations were named M1, M5, M12, M35, M37, M41, M57, M67, M81, M82, M84, M91, M99, M102, M111, M122, M126, M130, M135 and M145, which included sequentially the amino acid sequences as set forth in any one of SEQ ID NO: 1-20, respectively. At the same time, these mutants comprised sequentially the following combinations of amino acid mutations on the basis of the amino acid sequence as set forth in SEQ ID NO: 63:

(1) I61L, V63I, E77I, E84K, V93L, L96S, K98R, N100G and V132L;

(2) I61V, E77N, Q82S, K83R and E84H;

(3) I61F, V63I, K83R, E84K and V132I;

(4) I61L, E77Q, E84D, R107N and V132I;

(5) I61L, V63I, E77K, K83R, E84D and N100G;

(6) I61V, E77H, Q82R, K83R, E84H and R107S;

(7) I61L, E77I, Q82G, E84R, V93L, L96T, N100G, R107S, G109R and V132R;

(8) I61L, E77M, Q82G, K83R, E84D and V132L;

(9) I61L;

(10) I61F, D95H, L96S, G109H and V132S;

(11) I61F, D95H, L96S, K98R, G109H and V132S;

(12) I61L, E77Q, E84D, V93A, R107N and V132I;

(13) E77K, L96S, N100K, G109H and V132L;

(14) I61L, V63I, Q82G, E84G, D95R, L96S, N100D and V132I;

(15) I61L, E77R, Q82N, K83R, E84G, V93L, D95E, L96T, K98R, N100D and V132L;

(16) I61V, E77N, Q82S, K83R, E84H and V93A;

(17) I61V, V63I, E77V, K83R, E84D, D95E, L96T, K98R and N100E;

(18) I61L, V63I, E77V, K83R, D95E, L96S, K98R, N100D and G109R;

(19) I61V, E77L, Q82G, E84G, V93L, D95E, L96T, K98R and N100G; and

(20) I61L, V63I, E77N, Q82G and E84G.

Example 2 Measurement of Binding Activity of Fusion Protein

The truncated domain of human SIRPα variant 1 (or called wild-type SIRPα truncated domain) in Example 1 and the mutant of human SIRPα domain obtained in Example 1 (i.e., M1, M5, M12, M35, M37, M41, M57, M67, M81, M82, M84, M91, M99, M102, M111, M122, M126, M130, M135 and M145) were fused and expressed with the human IgG1-Fc (the amino acid sequence of which was set forth in SEQ ID NO: 67) respectively, so as to give the corresponding truncated domain-human Fc fusion protein of SIRPα mutant 1 (briefly, fusion protein). These fusion proteins were named SS002, SS002M1, SS002M5, SS002M12, SS002M35, SS002M37, SS002M41, SS002M57, SS002M67, SS002M81, SS002M82, SS002M84, SS002M91, SS002M99, SS002M102, SS002M111, SS002M122, SS002M126, SS002M130, SS002M135 and SS002M145, respectively. These fusion proteins comprised the amino acid sequence as set forth in any one of SEQ ID NO: 61 and 21-40, respectively.

TABLE 1

The Truncated Domain of SIRPα Mutant 1 and Mutant and Corresponding Fusion Protein

| Truncated Domain of SIRPα Mutant 1 or Its Mutant | Fusion Protein |
|---|---|
| Wild type SIRPα truncated domain | SS002 |
| M1 | SS002M1 |
| M5 | SS002M5 |
| M12 | SS002M12 |
| M35 | SS002M35 |
| M37 | SS002M37 |
| M41 | SS002M41 |
| M57 | SS002M57 |
| M67 | SS002M67 |
| M81 | SS002M81 |
| M82 | SS002M82 |
| M84 | SS002M84 |
| M91 | SS002M91 |
| M99 | SS002M99 |
| M102 | SS002M102 |
| M111 | SS002M111 |
| M122 | SS002M122 |
| M126 | SS002M126 |
| M130 | SS002M130 |
| M135 | SS002M135 |
| M145 | SS002M145 |

As an example, the fusion proteins SS002, SS002M12, SS002M5, SS002M82, SS002M84, SS002M91, SS002M102, and SS002M130 were selected for biological activity analysis.

The affinity of various fusion proteins including SS002, SS002M5, SS002M12, SS002M82, SS002M84, SS002M91, SS002M102, SS002M130 and the like to CD47 was determined via an ELISA method.

The ELISA plate was coated with 1 g/ml target antigen CD47-His at 4° C. overnight. After washing with PBST, 10% fetal bovine serum was added and the mixture was blocked at 37° C. for 1 hour. Then, SS002, SS002M5, SS002M82, SS002M84, SS002M91, SS002M102, and SS002M130 were added thereto, respectively, and reacted at 37° C. for 1 hour. Then, the reaction mixture was washed with PBST, and horseradish peroxidase-labeled Goat Anti human IgG HRP (Thermo Fisher Scientific) was added and reacted at room temperature for 30 minutes. Then, the plate was repeatedly washed with PBST for 5 times, and dried to remove the residual liquid as possible with absorbent paper. Next, 100 ml of TMB (eBioscience) was added to each well, and stood at room temperature (20±5° C.) in the dark for 1-5 min. 100 mL of 2N H2504 was added into each well to quench the substrate reaction. The OD value was read at 450 nm with a microplate reader, and the affinity between each fusion protein and CD47 molecule was analyzed (as shown in FIG. 5).

Figure 5:
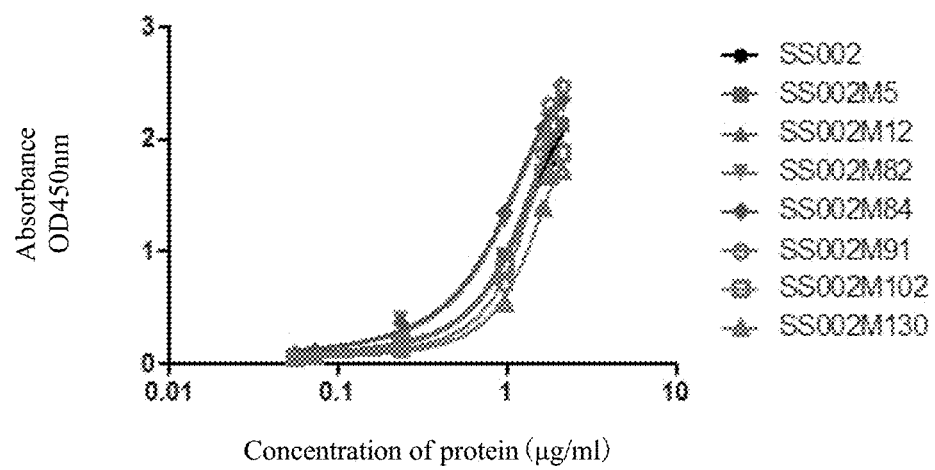
FIG. 5 shows the results of the fusion protein of the present application for recognizing the CD47 protein.

The results in FIG. 5 showed that various fusion proteins including SS002, SS002M5, SS002M12, SS002M82, SS002M84, SS002M91, SS002M102, SS002M130 and the like can effectively recognize the CD47 molecule.

Example 3 Analysis of Affinity

As an example, the Biacore method was used to measure the affinity of each fusion protein including SS002, SS002M5, SS002M12, SS002M82, SS002M84, SS002M91, SS002M102, SS002M130 and the like to the CD47 molecule, and the results were shown in Table 2 below.

TABLE 2

| Fusion Protein | Binding Affinity to CD47 | | |
| --- | --- | --- | --- |
| | $K_a$ ($10^6$ 1/Ms) | $K_d$ ($10^{-4}$ 1/s) | $K_D$ ($10^{-9}$ M) |
| SS002 | 1.32 ± 0.09 | 63.00 ± 1.35 | 4.80 ± 0.20 |
| SS002M5 | 1.72 ± 0.12 | 86.20 ± 9.65 | 5.00 ± 0.22 |
| SS002M12 | 1.87 ± 0.05 | 86.10 ± 2.94 | 4.62 ± 0.08 |
| SS002M82 | 1.29 ± 0.05 | 21.13 ± 0.42 | 1.65 ± 0.03 |
| SS002M84 | 1.10 ± 0.02 | 14.30 ± 0.20 | 1.30 ± 0.02 |
| SS002M91 | 1.56 ± 0.13 | 2.72 ± 0.44 | 0.18 ± 0.04 |
| SS002M102 | 1.79 ± 0.20 | 28.97 ± 7.83 | 1.60 ± 0.24 |
| SS002M130 | 1.43 ± 0.09 | 88.20 ± 8.67 | 6.20 ± 0.99 |

The results in Table 2 showed that SS002, SS002M5, SS002M12, SS002M82, SS002M84, SS002M91, SS002M102, SS002M130 and other fusion proteins can recognize CD47 molecules with high affinity.

Example 4 Specificity of Species Recognition of Fusion Protein

Fusion proteins SS002 and SS002M91 were taken as examples to perform an analysis of the specific recognition activity.

For carrying out the species analysis of the fusion proteins, 1 mg/mL human CD47 and mouse CD47 (Beijing Yiqiao Shenzhou Biotechnology Co., Ltd.) were coated on ELISA plates, respectively, and stood at 4° C. overnight. After washing with PBST, 10% fetal bovine serum was added, and the mixture was blocked at 37° C. for 1 hour. Then, SS002 and SS002M91 were added, respectively, and reacted at 37° C. for 1 hour. After washing with PBST, horseradish peroxidase-labeled Goat Anti human IgG HRP (Thermo Fisher Scientific) was added and reacted at room temperature for 30 minutes. Then, the plate was repeatedly washed with PBST for 5 times, and dried to remove the residual liquid drops as possible with absorbent paper. Then, 100 ml TMB (eBioscience) was added to each well, and stood at room temperature (20±5° C.) in the dark for 1-5 min. 100 mL of 2N H2504 was added to each well to quench the substrate reaction. The OD value was read at 450 nm with a microplate reader, and the binding ability of the fusion protein to different species of CD47 was analyzed (the experimental results of the fusion protein SS002 and SS002M91 were shown in FIGS. 6A and 6B, respectively).

Figure 6A:
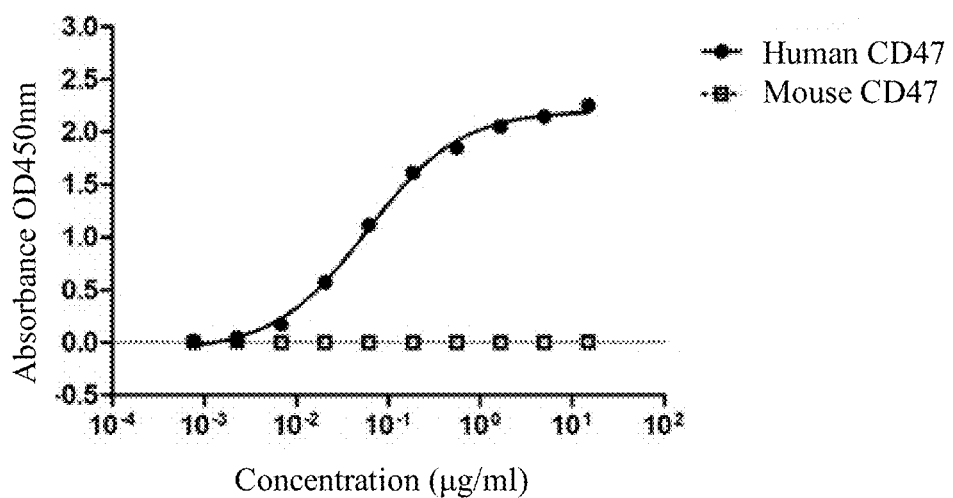
FIGS. 6A-6B show the specificity of the fusion protein of the present application for recognizing a human CD47 protein.
Figure 6B:
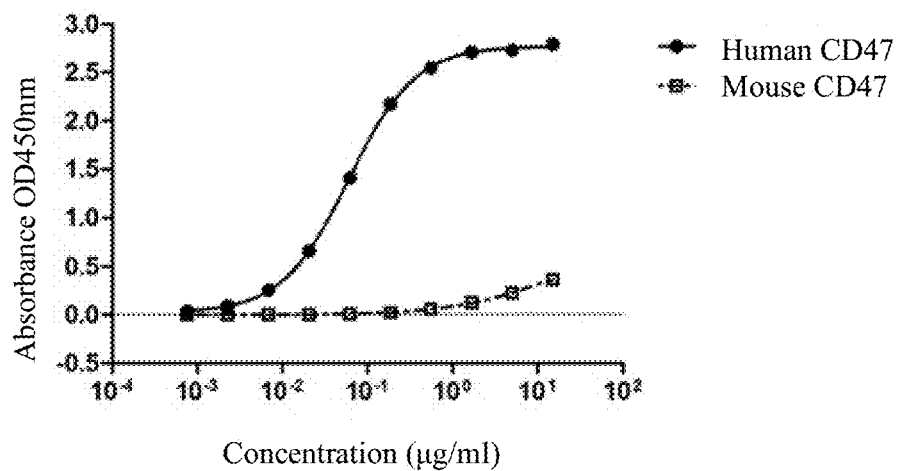

The results of FIGS. 6A-6B showed that both SS002 and SS002M91 can specifically recognize human CD47 molecules, but cannot recognize mouse CD47 molecules.

Example 5 the Fusion Proteins Specifically Recognize Target Antigen

The fusion proteins SS002 and SS002M91 were taken as examples. 1 mg/ml of SS002, SS002M91, as well as Milk (Beijing Bomed Biotechnology Co., Ltd.), BSA (BOVOGEN), CD19 (Beijing Yiqiao Shenzhou Biotechnology Co., Ltd.), TROP2 (Beijing Yiqiao Shenzhou Biotechnology Co., Ltd.), CD47 (Beijing Magppel Biotech Co., Ltd.), CD38 (Beijing Yiqiao Shenzhou Biotechnology Co., Ltd.), Gas6 (R&D) and other proteins, and AXL (ACRO Biosystems) were coated on ELISA plates, respectively, and stood at 4° C. overnight. After washing with PBST, 10% fetal bovine serum was added, and the mixture was blocked at 37° C. for 1 hour. Then, SS002 and SS002M91 were added, respectively, and reacted at 37° C. for 1 hour. After washing with PBST, horseradish peroxidase-labeled Goat Anti human IgG HRP (Thermo Fisher Scientific) was added and reacted at room temperature for 30 minutes. Then, the plate was repeatedly washed with PBST for 5 times, and dried to remove the residual liquid drops as possible with absorbent paper. Then, 100 ml TMB (eBioscience) was added to each well, and stood at room temperature (20±5° C.) in the dark for 1-5 min. 100 mL of 2N H2504 was added to each well to quench the substrate reaction. The OD value was read at 450 nm with a microplate reader, and the binding ability of the fusion protein to various foresaid protein was analyzed (as shown in FIG. 7).

Figure 7:
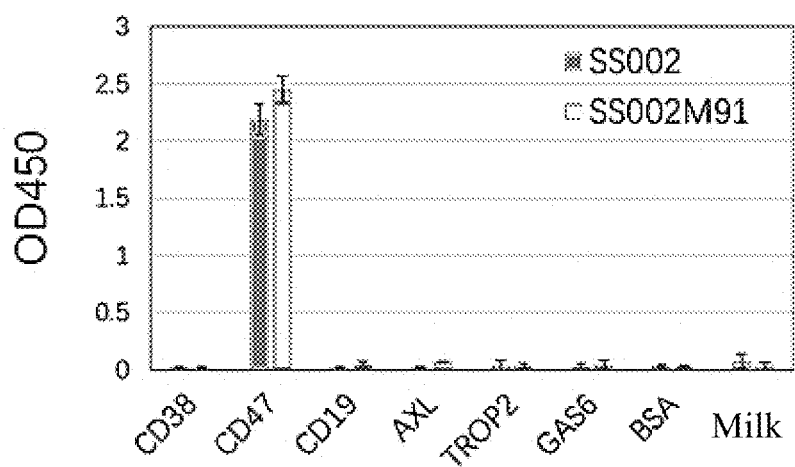
FIG. 7 shows the recognition of the fusion protein of the present application for a human CD47 protein and other proteins.

The results in FIG. 7 showed that the fusion proteins SS002 and SS002M91 merely recognize the human CD47 molecule, and do not undergo any cross-reaction with other various proteins.

Example 6 the Fusion Proteins Specifically Block the CD47/SIRPα Interaction

SS002M91 was taken as an example to perform the analysis of specifically blocking the CD47/SIRPα interaction activity, and the expression of American congener TTI-621 (see CN105073780A) was used as a positive control.

1 μg/ml SIRPα-His was coated on the ELISA plate and stood at 4° C. overnight. After washing with PBST, 10% fetal bovine serum was added and the mixture was blocked at 37° C. for 1 hour. SS002M91 and TTI-621 were serially diluted with 10% fetal bovine blood, respectively, and Biotin-Fc-CD47 was added to the samples to a final concentration of 2 μg/ml. The mixture was pre-incubated at 37° C. for 30 min for use as the primary antibody. After the ELISA plate was washed with PBST, the primary antibody was added and incubated at 37° C. for 1 hour. Then, after washing with PBST for 5 times, horseradish peroxidase-labeled avidin (Streptavidin-HRP, Jiaxuan Bio) was added, and incubated at 37° C. for 30 minutes. After washing with PBST for 5 times, 100 μL of TMB (eBioscience) was added into each well, and stood at room temperature (20±5° C.) in the dark for 1-5 min. 100 μL of 2N $H_2SO_4$ was added to each well to quench the substrate reaction. The OD value was read at 450 nm with a microplate reader, and the blocking effect of SIRPα fusion protein on CD47/SIRPα was analyzed (as shown in FIG. 8).

Figure 8:
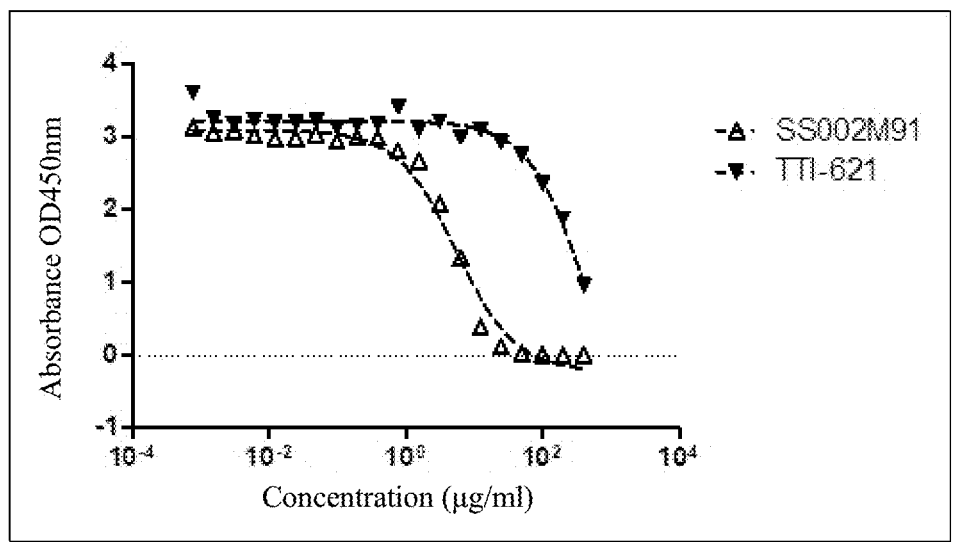
FIG. 8 shows that the fusion protein of the present application and TTI-621 competitively block the binding of the CD47 protein to its ligand SIRPα.

The results in FIG. 8 showed that both SS002M91 and TTI-621 can competitively block the binding of CD47 to its ligand SIRPα. However, the fusion protein SS002M91 has a significantly higher blocking activity than TTI-621. The IC50 value of SS002M91 is 5.47 μg/mL, while the IC50 value of TTI-621 is 493.5 μg/mL.

Example 7 the Fusion Protein Specifically Recognize the CD47 Molecule on the Surface of Tumor Cells The fusion proteins SS002 and SS002M91 were taken as examples to analyze the recognition activity of the CD47 molecule on the surface of tumor cells.

Figure 9A:
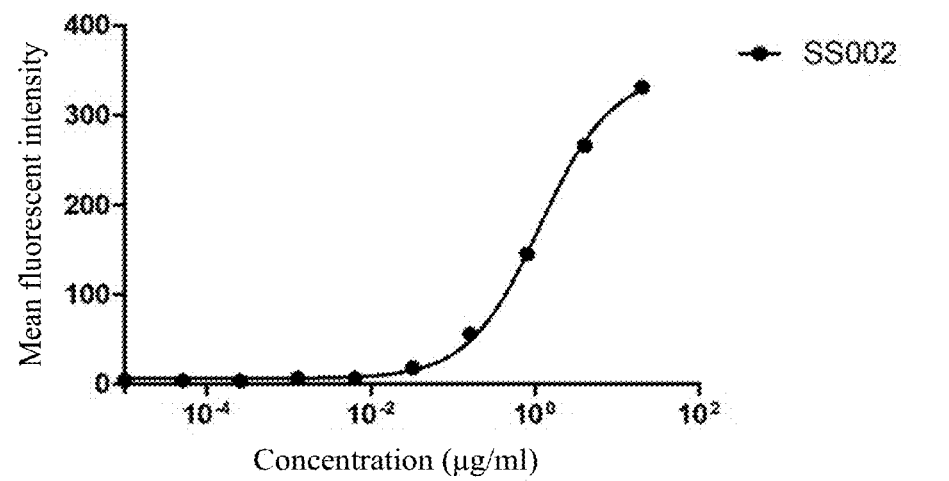
FIGS. 9A-9C show the results of the fusion protein of the present application for recognizing Raji cell, Jurkat cell and the surface CD47 protein of A549 cell.
Figure 9A:
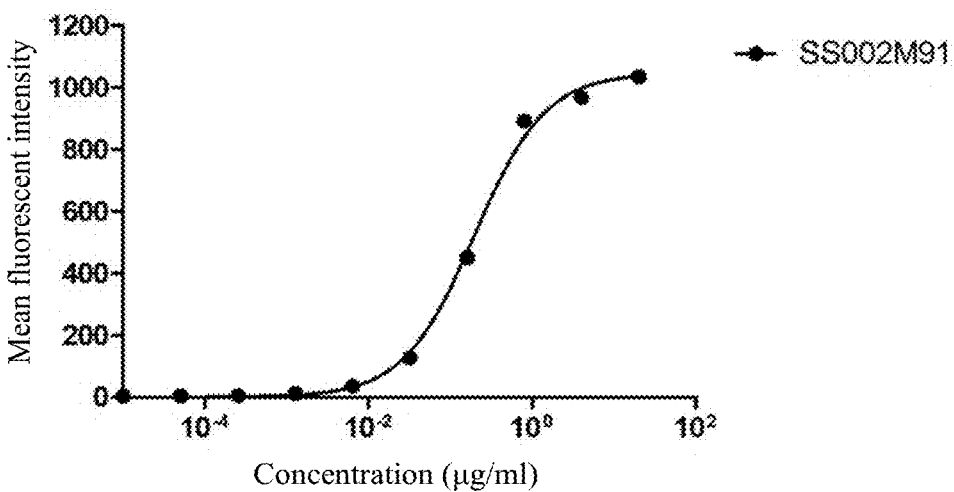
Figure 9B:
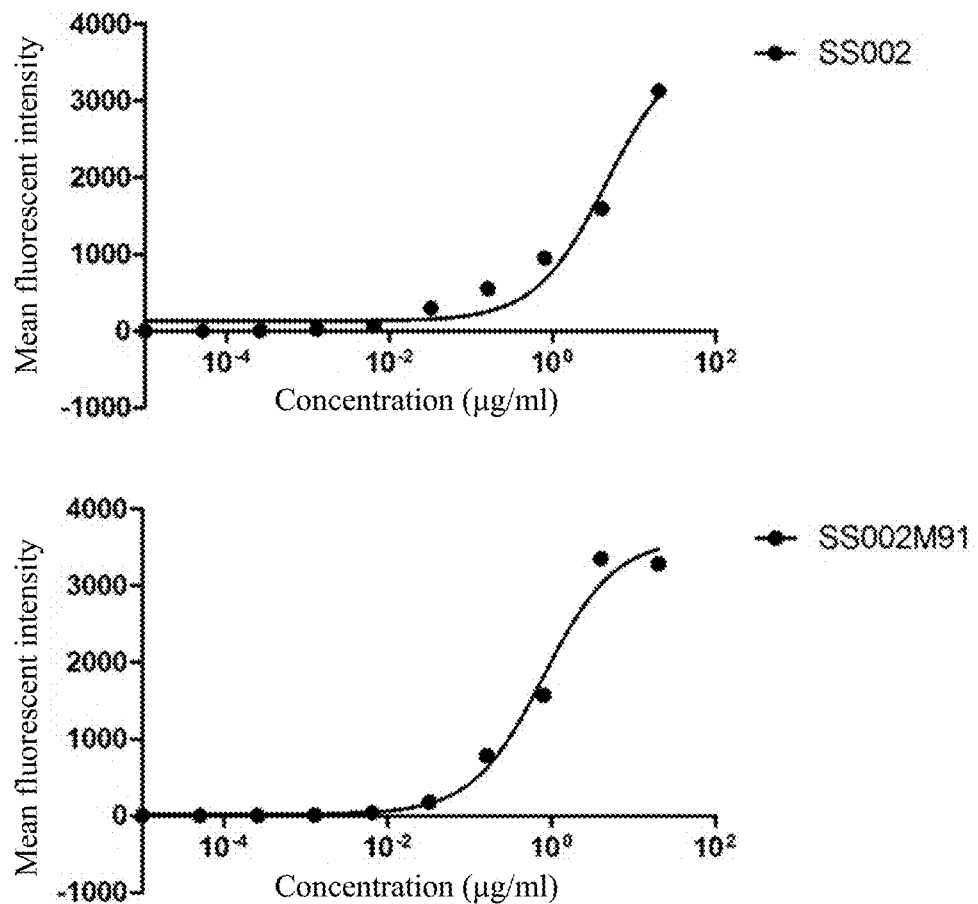
Figure 9C:
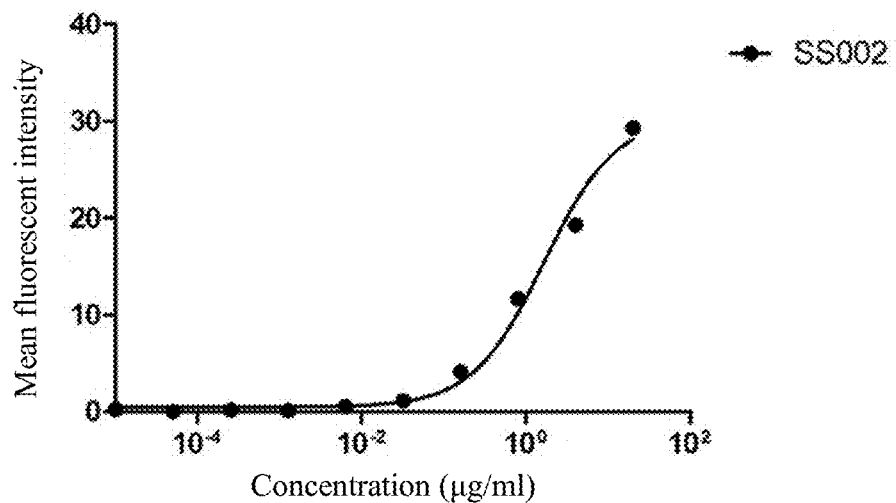
Figure 9C:
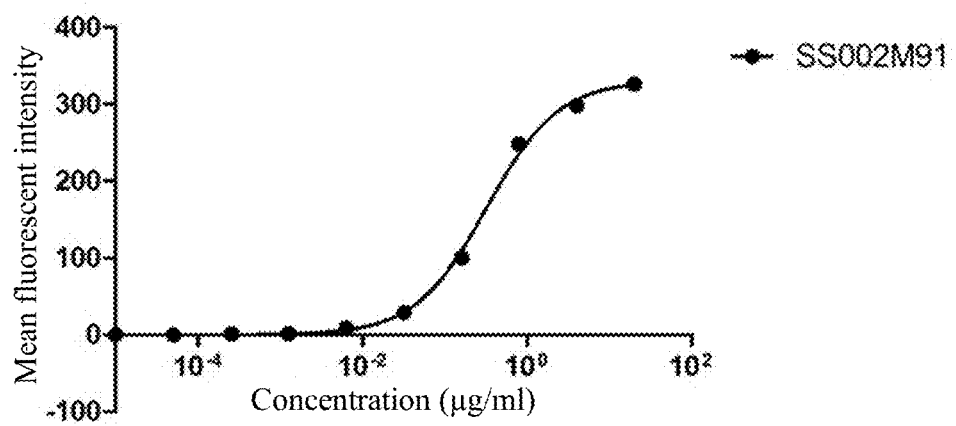

Flow cytometry (BD Calibur) was used to respectively detect the activities of SS002 and SS002M91 that specifically recognized the CD47 molecules on the surface of Raji cells, Jurkat cells and A549 cells. The aforementioned cells in the logarithmic growth phase were collected, respectively, adjusted to a cell density to $5 \times 10^6$ cells/mL, and pre-cooled on ice for 10 minutes. The SIRPα fusion proteins SS002 and SS002M91 were diluted to different concentrations with pre-cooled normal saline containing 2% FBS. 100 μL of cells were added into an equal volume of the aforementioned diluted SIRPα fusion protein, and reacted at 4° C. in the dark for 30 min. After completion, the cells were washed twice with pre-cooled normal saline containing 2% FBS. The cells were re-suspended in 100 μL of diluted PE-goat anti-human IgG-Fc secondary antibody (eBioscience), and reacted at 4° C. in the dark for 30 min. After completion of the reaction, the cells were washed twice with pre-cooled normal saline containing 2% FBS, and resuspended in 400 μL of 1% paraformaldehyde. Flow cytometry (BD Calibur) was used to analyze the binding ability of the fusion protein to CD47 on the surface of cells (as shown in FIGS. 9A-9C which showed that the fusion proteins SS002 and SS002M91 specifically recognize the surface CD47 of Raji cells, Jurkat cells and A549 cells, respectively).

The results showed that the fusion protein SS002M91 can specifically recognize CD47 on the surface of Raji cells, Jurkat cells and A549 cells with a recognition activity that was significantly higher than that of SS002 and presented a dose-dependency. Among them, the EC50 value of binding to Raji cells was 197.0 ng/mL for SS002M91 and 1140.0 ng/mL for SS002 (as shown in FIG. 9A). For the EC50 value of binding to Jurkat cells, SS002M91 was 796.0 ng/mL and SS002 was 4529.0 ng/mL (as shown in FIG. 9B). For the EC50 value of binding to A549 cells, SS002M91 was 321.9 ng/mL, and SS002 was 1655.0 ng/mL (as shown in FIG. 9C).

Figure 10A:
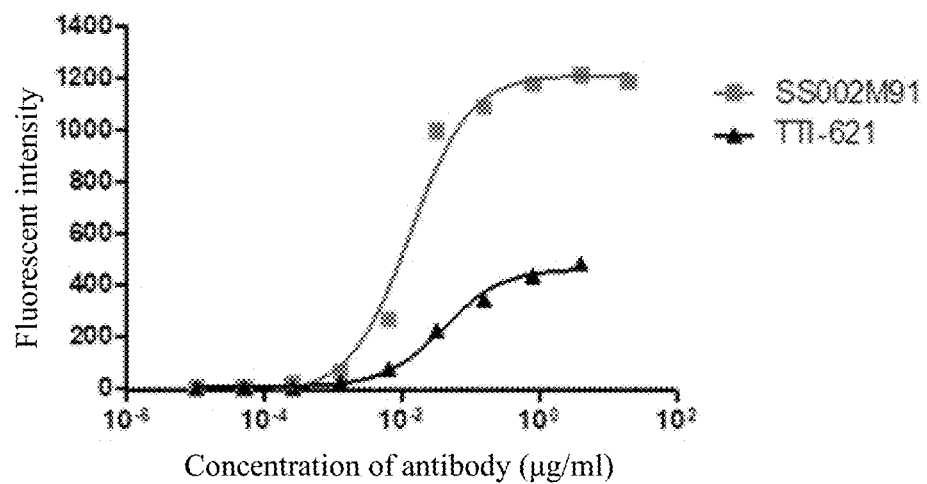
FIGS. 10A-10C show the results of the fusion protein of the present application and TTI-621 for recognizing Raji cell, Jurkat cell and the surface CD47 protein of A549 cell.
Figure 10B:
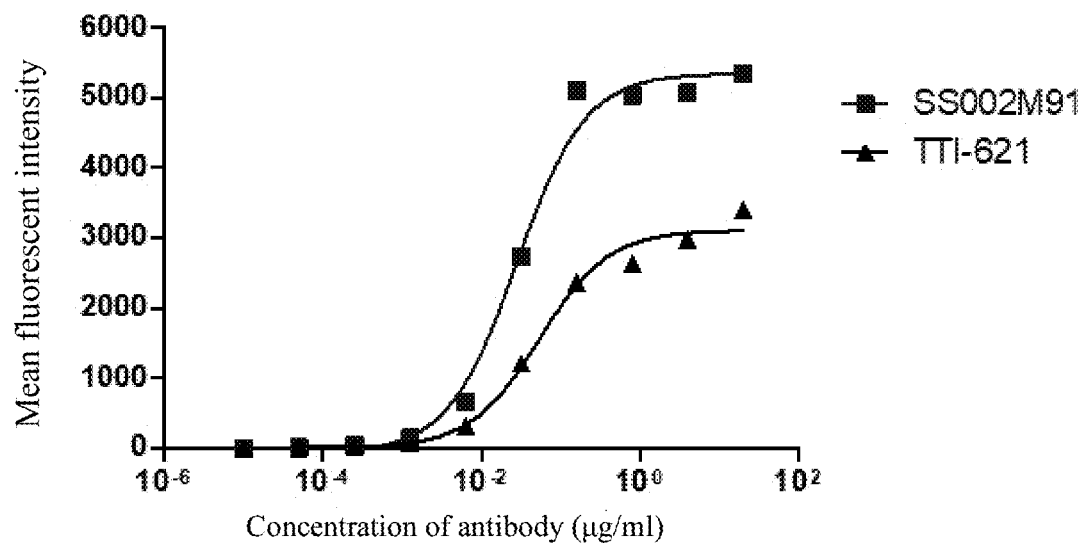
Figure 10C:
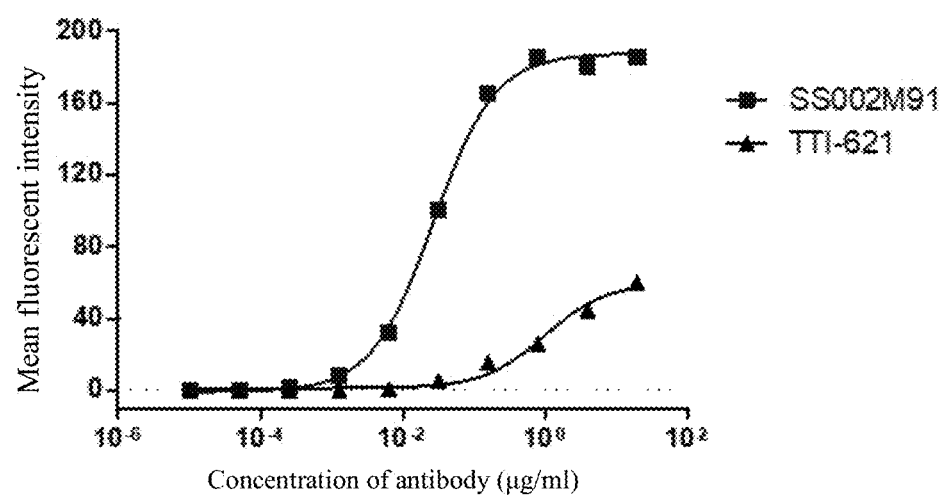

Likewise, the method of this example was used to compare the activities of SS002M91 and TTI-621 for recognizing CD47 molecules on the cell surfaces of Raji cells (as shown in FIG. 10A), Jurkat cells (as shown in FIG. 10B), and A549 cells (as shown in FIG. 10C). The results showed that, in one aspect, the maximum fluorescence intensity of SS002M91 that specifically recognizes the CD47 molecules on the surface of tumor cells was significantly higher than that of TTI-621: the maximum fluorescence intensity of SS002M91 binding to Raji cells was about 1200, while the maximum fluorescence intensity of TTI-621 binding to Raji cells was about 600; the maximum fluorescence intensity of SS002M91 binding to Jurkat cells was about 5000, while the maximum fluorescence intensity of TTI-621 binding to Jurkat cells was about 3000; the maximum fluorescence intensity of SS002M91 binding to A549 cells was about 180, while the maximum fluorescence intensity of TTI-621 binding to A549 cells was about 60. In another aspect, the half-optimal dose of SS002M91 that specifically recognized the CD47 molecules on the surface of tumor cells was significantly superior to TTI-621: the EC50 value of SS002M91 binding to Raji cells was 13.06 ng/mL, while the EC50 value of TTI-621 binding to Raji cells was 40.37 ng/Ml; the EC50 value of SS002M91 binding to Jurkat cells was 28.09 ng/mL, while the EC50 value of TTI-621 binding to Jurkat cells was 53.92 ng/Ml; the EC50 value of SS002M91 binding to A549 cells was 26.95 ng/mL, and the EC50 value of TTI-621 binding to A549 cells was 1003 ng/mL. It could be seen that SS002M91 that specifically recognizes CD47 molecules on the surface of tumor cells is significantly better than TT1-621.

Example 8 Detection of Blood Clotting Reaction

SS002 and SS002M91 were taken as examples to perform the analysis of blood clotting activity, using the CD47 antibody Hu5F9-G4 as control (see Guerriero J L, Sotayo A, Ponichtera H E, et al. Class IIa HDAC inhibition reduces breast tumors and metastases through anti-tumour macrophages. [J] Nature, 2017, 543(7645): 428.432 and Gholamin S, Mitra S S, Feroze A H et al. Disrupting the CD47-SIRPα anti-phagocytic axis by a humanized anti-CD47 antibody is an efficacious treatment for malignant pediatric brain tumors. Sci. Transl. Med 2017).

A whole blood from healthy donors was used to prepare human red blood cells (collected from peripheral blood of volunteers). The whole blood was diluted for 5 times with PBS, washed for 3 times, and prepared into a fresh 1% solution of red blood cells. 50 μL of different concentrations of SIRPα fusion proteins SS002, SS002M91 and anti-CD47 antibody Hu5F9-G4 were added to each well of the hemagglutination plate, and then 50 μL of 1% red blood cell solution was added to each well. The mixture was gently mixed to uniform, and incubated at 37° C. under 5% CO2 overnight. Then, the plate was photographed for interpretation by use of the standards that all the red blood cells coagulated, sunk to the bottom of the well, and flattened in a mesh shape as 100% coagulation (++++) and the phenomenon that the red blood cells sunk to the bottom of the well and presented dot-like as no coagulation (−) (as shown in FIG. 11).

Figure 11:
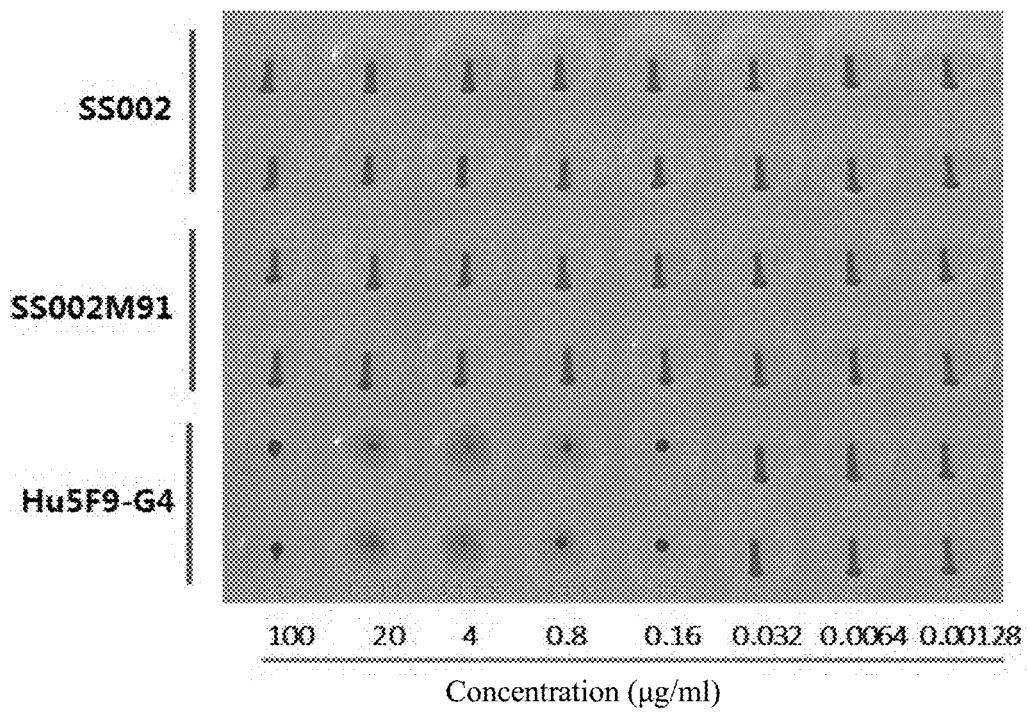
FIG. 11 shows the results of the fusion protein of the present application and Hu5F9-G4 for resisting the blood clotting reaction.

The results in FIG. 11 showed that the fusion proteins SS002M91 and SS002 do not induce red blood cell agglutination, while the CD47 antibody Hu5F9-G4 can significantly cause red blood cell agglutination within a certain dose range.

Example 9 Detection of In Vivo Tumor-Inhibiting Activity

The fusion protein SS002M91 was taken as an example to analyze the in vivo tumor-inhibiting activity.

B-NSG mice were inoculated with Raji-Luc cells to establish a tumor model to evaluate the tumor-inhibiting activity of SS002M91 antibody. Female, 8-week-old B-NSG mice (Beijing Biocytogene Biotechnology Co., Ltd.) were taken as experimental animals and Raji-Luc cell (Beijing Biocytogene Biotechnology Co., Ltd.) were selected for testing. The Raji-Luc cells were transferred into the stable cell line obtained by the fluorescein reporter gene. After resuscitating and culturing to the required number, the log-phase growth cells were collected and suspended to a concentration of $5 \times 10^6$ cells/0.2 mL. Then, the B-NSG mice were inoculated via the tail vein at 0.2 mL/mouse. After inoculation, the tumor growth and body weight were observed on Day 0 and Day 3 with a small animal imager.

Figure 12A:
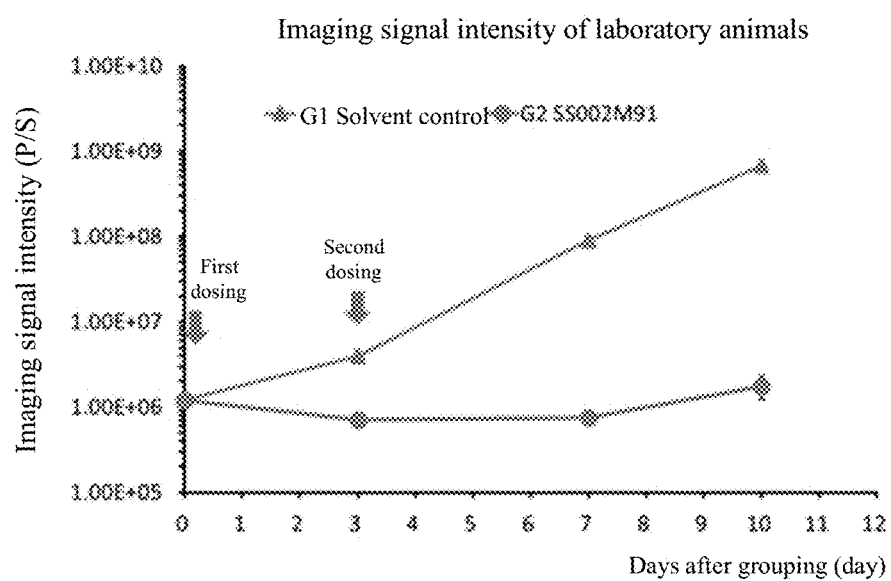
FIGS. 12A-12B show the tumor-inhibiting activity of the fusion protein of the present application.
Figure 12B:
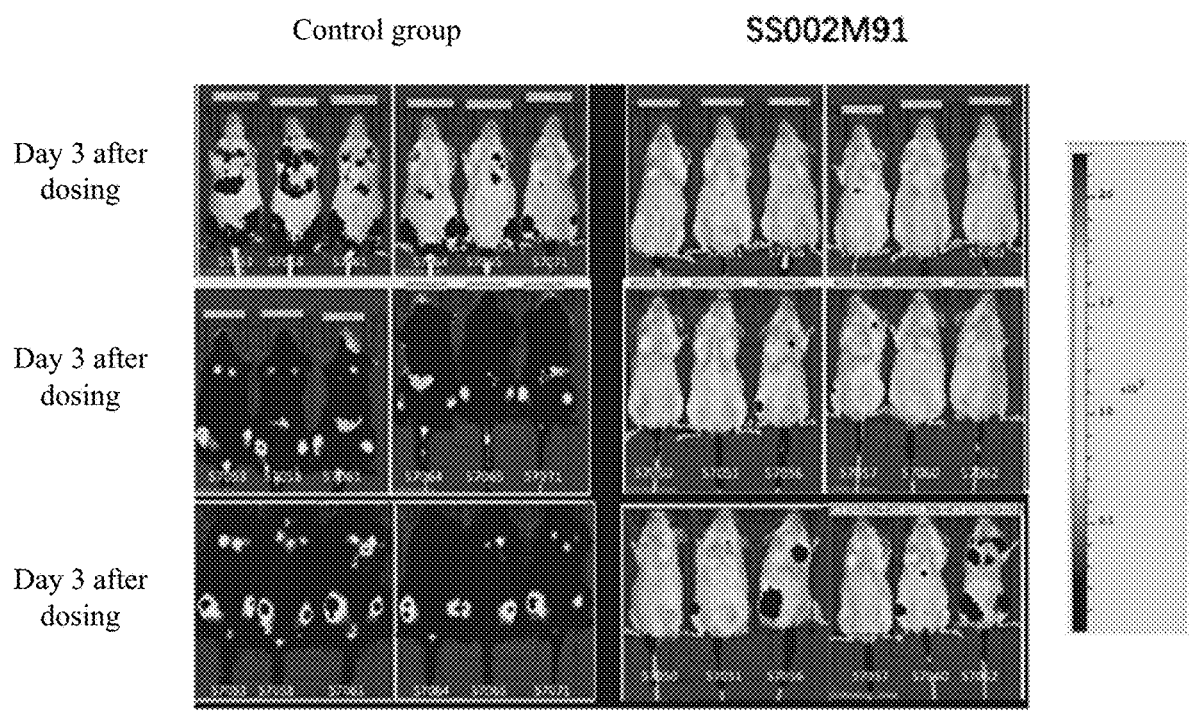

And on Day 3, 12 mice with moderate tumors imaging signal (about $1.00\times10^6$ P/S) were selected and randomly divided into 2 groups (6 mice per group), that is, solvent control group (G1, normal saline) and experimental group (G2, SS002M91). The experimental group was administered at a dose of 10 mg/kg on Day 0 and D3 after grouping, twice in total. The tumor growth of the mice and the survival rate of mice were observed (as shown in FIGS. 12A and 12B respectively).

The results showed that on Day 10 after grouping, the control group exhibits a mean fluorescence intensity of tumors of $6.75\times10^8$ P/S, while the dosing group exhibits a mean fluorescence intensity of tumors of $1.76\times10^6$ P/S and an inhibit rate of about 95%.

Example 10 Detection of Effects on Red Blood Cells and Platelets

The fusion protein SS002M91 was taken as an example, and B-NSG mice were used as a model to perform a preliminary evaluation of in vivo safety.

Figure 13A:
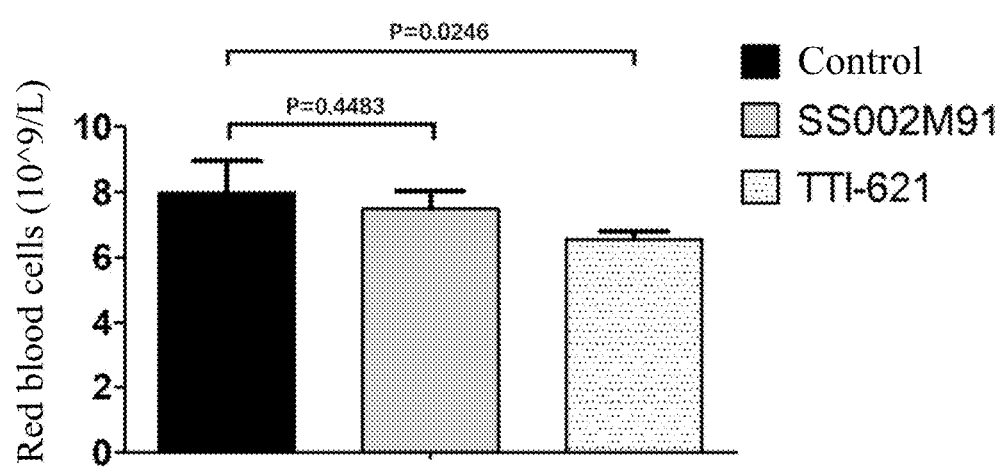
FIGS. 13A-13B show the effects of the fusion protein of the present application on red blood cells and platelets as compared with TTI-621.
Figure 13B:
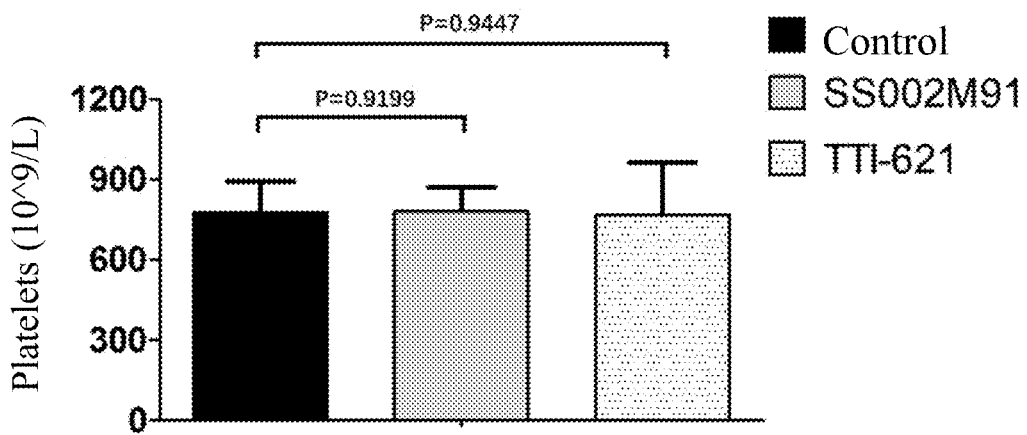

18 female, 8-week-old B-NSG mice (Beijing Biocytogene Biotechnology Co., Ltd.) were selected and randomly divided into 3 groups, that is, a solvent control group (administered with normal saline), an experimental group (administered with the fusion protein SS002M91) and a positive control group (administered with TTI-621) (6 mice per group). The mice were administered at a dose of 10 mg/kg on Day 0 and Day 3 and Day 7 after grouping, 3 times in total. On the day next to the third administration (i.e., Day 8), the peripheral blood of the mice was analyzed for the levels of red blood cell and platelet (the red blood cell level and the platelet level are shown in FIG. 13A and FIG. 13B, respectively).

The results showed that as compared with the control group, SS002M91 does not cause a significant decrease in red blood cells (P=0.4483) and platelets (P=0.9199); while TTI-621 had a small effect on platelets (P=0.9447), but caused a decrease in red blood cells (P=0.0246).

Example 11 Effect of Fusion with Different Subtypes of IgG Fc on Activity of Fusion Protein According to the method of constructing the fusion protein in Example 2, the mutants M1, M5, M12, M35, M37, M41, M57, M67, M81, M82, M84, M91, M99, M102, M111, M122, M126, M130, M135 and M145 of the SIRPα domain obtained in Example 1 were fused and expressed with human IgG4-Fc (of which the amino acid sequences were set forth in SEQ ID NO: 68), respectively, to obtain the corresponding SIRPα mutant 1 truncated domains-human Fc fusion protein (referred to as fusion protein). These fusion proteins were named SS002M1G4, SS002M5 G4, SS002M12G4, SS002M35G4, SS002M37G4, SS002M41G4, SS002M57G4, SS002M67G4, SS002M81G4, SS002M82G4, SS002M84G4, SS002M91G4, SS002M99G4, SS002M102G4, SS002M111G4, SS002M122G4, SS002M126G4, SS002M130G4, SS002M135G4 and SS002M145G4 (of which the amino acid sequences were set forth in SEQ ID NO: 41-60, respectively).

As an example, the fusion protein SS002M91G4 was selected for biological activity analysis.

Figure 14:
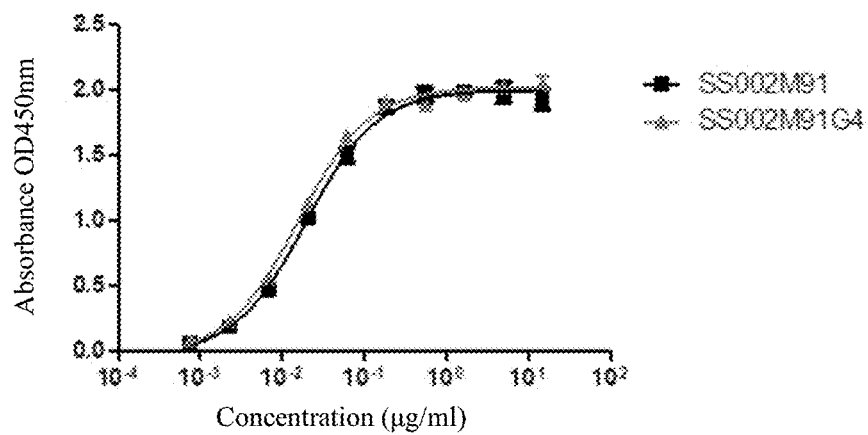
FIG. 14 shows the results of the fusion protein of the present application for recognizing the CD47 protein.

According to the method of measuring the binding activity in Example 2, the activity of SS002M91G4 binding to the antigen CD47 was analyzed, and the results were shown in FIG. 14. The results of FIG. 14 showed that SS002M91G4 has good activity to bind to the CD47 antigen with an EC50 value of 0.0157m/mL, that is substantially consistent with the EC50 (0.0195 μg/mL) of SS002M91.

Figure 15:
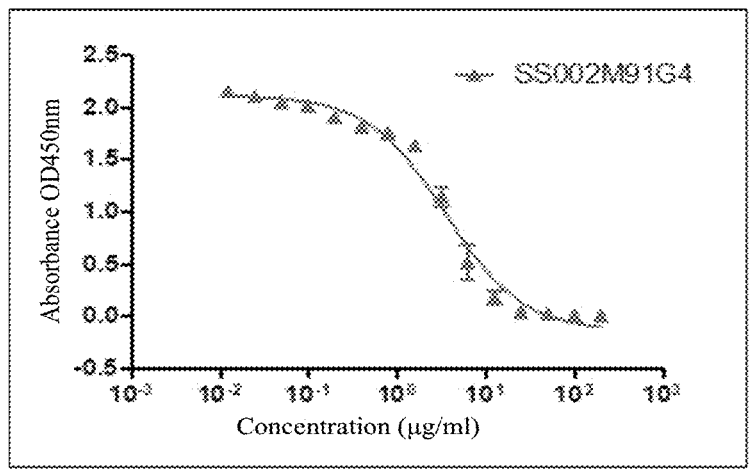
FIG. 15 shows that the fusion protein of the present application competitively blocks the binding of the CD47 protein to its ligand SIRPα.

According to the method of analyzing the specific blocking of the CD47/SIRPα interaction in Example 6, the activity of SS002M91G4 blocking the CD47/SIRPα interaction was analyzed, and the results were shown in FIG. 15. The results of FIG. 15 showed that SS002M91G4 has good activity of blocking the CD47/SIRPα interaction with an IC50 value of 3.46 μg/mL, which is substantially consistent with the IC50 value (5.47 μg/mL) of SS002M91.

It can be seen from the above results that the fusion of different subtypes of IgG Fc has no significant effect on the activity of the fusion protein constructed by the present application.

Example 12 Detection of Blood Clotting Reaction of Fusion Protein

Taking SS002M91G4 as an example, and by reference to the method of detecting the blood clotting reaction in Example 8, the blood clotting reaction of the fusion protein based on IgG4 Fc was evaluated. A whole blood from healthy donors was used to prepare human red blood cells. The whole blood was diluted for 5 times with PBS, washed for 3 times, and prepared into a fresh 1% solution of red blood cells. 50 μL of different concentrations of fusion proteins SS002M91G4, the positive control TTI-621 and anti-CD47 antibody Hu5F9-G4 were added to each well of the hemagglutination plate, and then 50 μL of 1% red blood cell solution was added to each well. The mixture was gently mixed to uniform, and incubated at 37° C. under 5% CO2 overnight. Then, the plate was photographed for interpretation by use of the standards that all the red blood cells coagulated, sunk to the bottom of the well, and flattened in a mesh shape as 100% coagulation (++++) and the phenomenon that the red blood cells sunk to the bottom of the well and presented dot-like as no coagulation (-).

Figure 16:
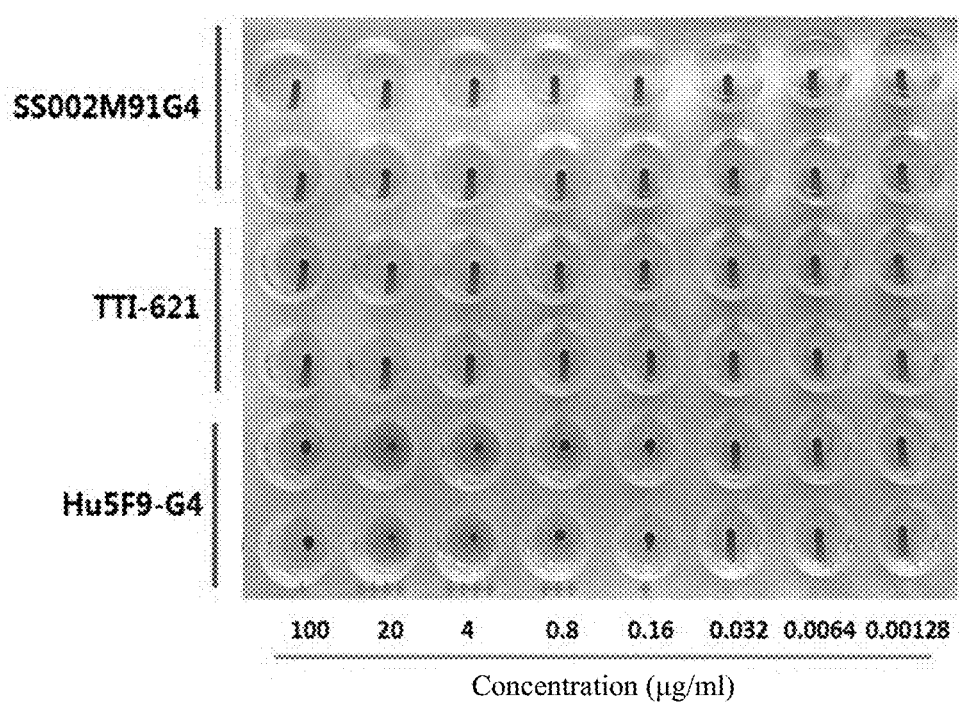
FIG. 16 shows the results of the fusion protein of the present application and Hu5F9-G4 for resisting the blood clotting reaction.

The results are shown in FIG. 16. The results showed that the fusion proteins SS002M91G4 and TTI-621 based on IgG4 Fc do not cause agglutination of red blood cells, while the CD47 antibody Hu5F9-G4 significantly caused agglutination of red blood cells within a certain dose range.

Example 13 Analysis of Biological Activity of Fusion Protein

Taking SS002M91G4 as an example, the Jurkat-CSR cell (Immune Onco Biomedical Technology (Shanghai) Co., Ltd.) system was used to evaluate the biological activity of said fusion protein based on IgG4 Fc by use of TTI-621 as positive control.

CD47-Fc protein (Cat #12283-H02H, Sino Biological) was diluted to 0.2m/mL, and 50 μL of protein diluent was added to each well. Then, TTI-621 and SS002M91G4 were diluted to 0.4 mg/mL, respectively, and then serially diluted to different concentrations. 504, was added to each well, and co-incubated with CD47-Fc in a 37° C., 5% $CO_2$ incubator for 45 min. Jurkat-CSR cells were taken and adjusted to a density of $5\times10^5$/mL, 1004, cell suspension was added to each well, while a blank control group was set. The suspension was co-cultured with the protein mixture in a 37° C., 5% CO2 incubator for 20 hours. After completion of culture, 20 μL of CCK-8 (Dojindo, Japan Institute of Chemistry) was added to each well, and cultured in a 37° C., 5% CO2 incubator for 4 hours. The OD value was measured at a wavelength of 450 nm with a microplate reader. The inhibition rate of cell growth was calculated in accordance with the following formula:

Inhibition Percent=(OD450 (sample)−OD450 (blank)/(OD450 (Jurkat-CSR)−OD450 (blank))× 100

Figure 17:
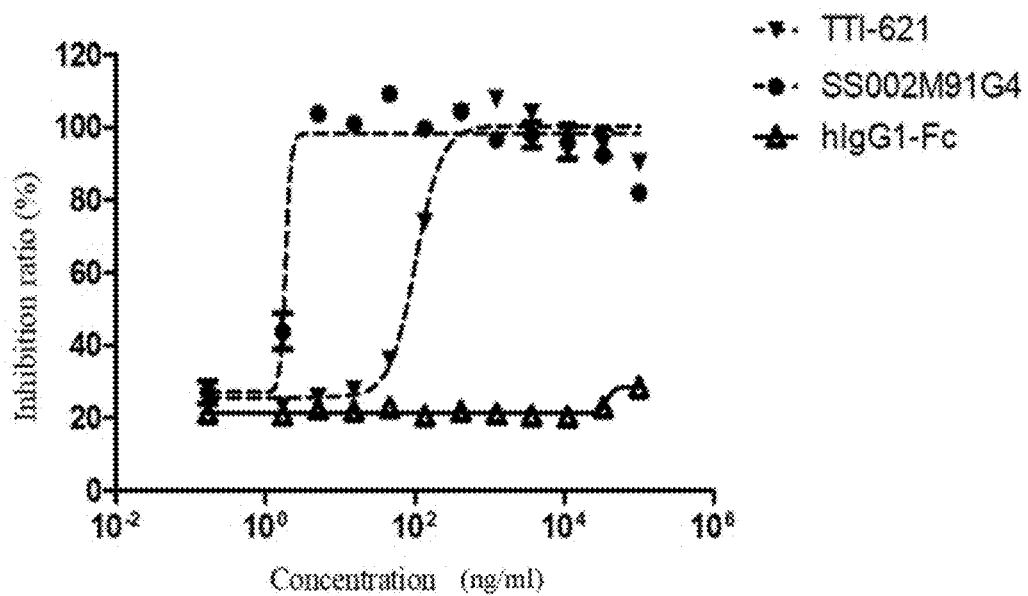
FIG. 17 shows that the fusion protein of the present application effectively blocks the CD47-Fc-induced apoptosis of Jurkat-CSR cell.

According to the principle of the Jurkat-CSR cell system, CD47/SIRPα interaction can induce apoptosis of target cells; and the addition of an inhibitor that inhibits the CD47/SIRPα interaction can block the apoptosis signal. The stronger the inhibitor's effect, the more fully the apoptotic signal is blocked. The result was shown in FIG. 17. The results showed that SS002M91G4 can significantly block the apoptosis of Jurkat-CSR cells induced by CD47-Fc, the blocking effect is stronger than that of TTI-621, and the IC50 is about 1/100 of TTI-621. It can be seen that the biological activity of SS002M91G4 in blocking CD47/SIRPα interaction is significantly better than that of TTI-621.

Example 14 In Vivo Tumor-Inhibiting Activity of Fc Fusion Protein of Different IgG Subtypes and Effect on Red Blood Cells and Platelets Taking the fusion proteins SS002M91 and SS002M91G4 as an example, the in vivo tumor-inhibiting activity and the effect on red blood cells and platelets were analyzed.

By subcutaneously inoculating Raji cells in NOD/SCID mice, a subcutaneous transplanted tumor model of human lymphoma was established to evaluate the in vivo tumor-inhibiting activity of SS002M91 and SS002M91G4.

Female, 6-7-week-old NOD/SCID mice (Shanghai Lingchang Biotechnology Co., Ltd.) were selected, and Raji cells were cultured in an RPMI1640 media containing 10% fetal bovine serum. $1 \times 10^7$ Raji cells in the exponential growth phase were collected and re-suspended to an appropriate concentration in PBS, and then mixed with matrigel (BD Matrigel™) at 1:1 for subcutaneous tumor inoculation of mice. After inoculation, when the average volume of tumors is about 98.6 mm$^3$, the mice were randomly divided into 4 groups (6 mice per group) according to the tumor size (that is, a vehicle control group, an SS002M91 group, an SS002M91G4 group, and a TTI-621 group). The mice were administered via intraperitoneal injection at a dose of 10 mg/kg per time (wherein the above 4 groups were administered with PBS solution, SS002M91, SS002M91G4 and TTI-621, respectively) and a frequency of twice a week, for a total of two weeks.

Figure 18A:
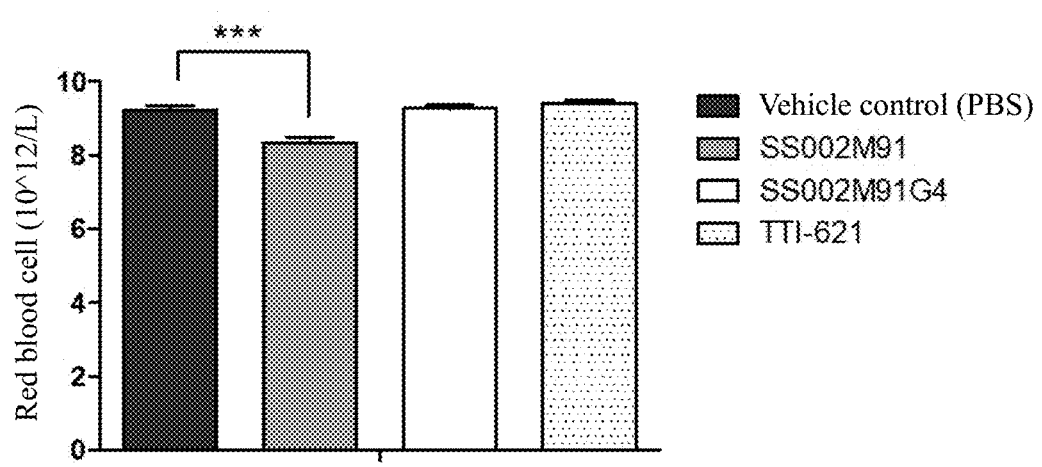
FIG. 18A shows the effects of the fusion protein of the present application on the level of red blood cells in the peripheral blood of mice.
Figure 18B:
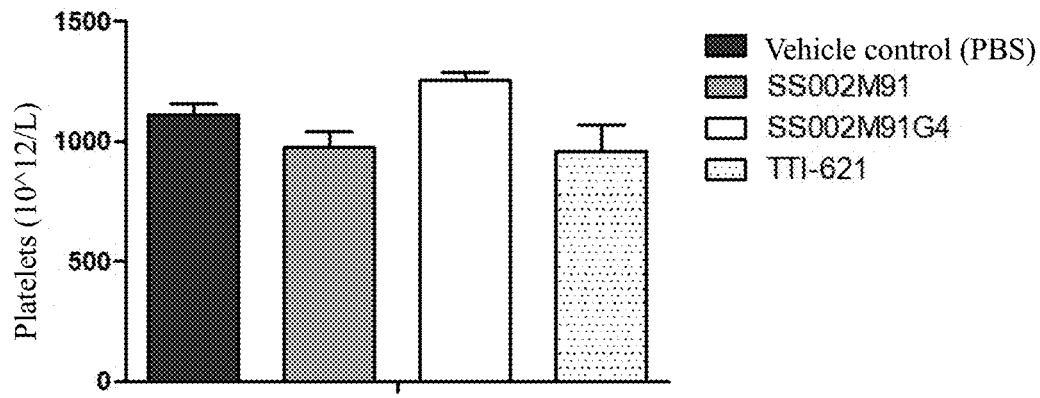
FIG. 18B shows the effects of the fusion protein of the present application on the level of platelets in the peripheral blood of mice.
Figure 19:
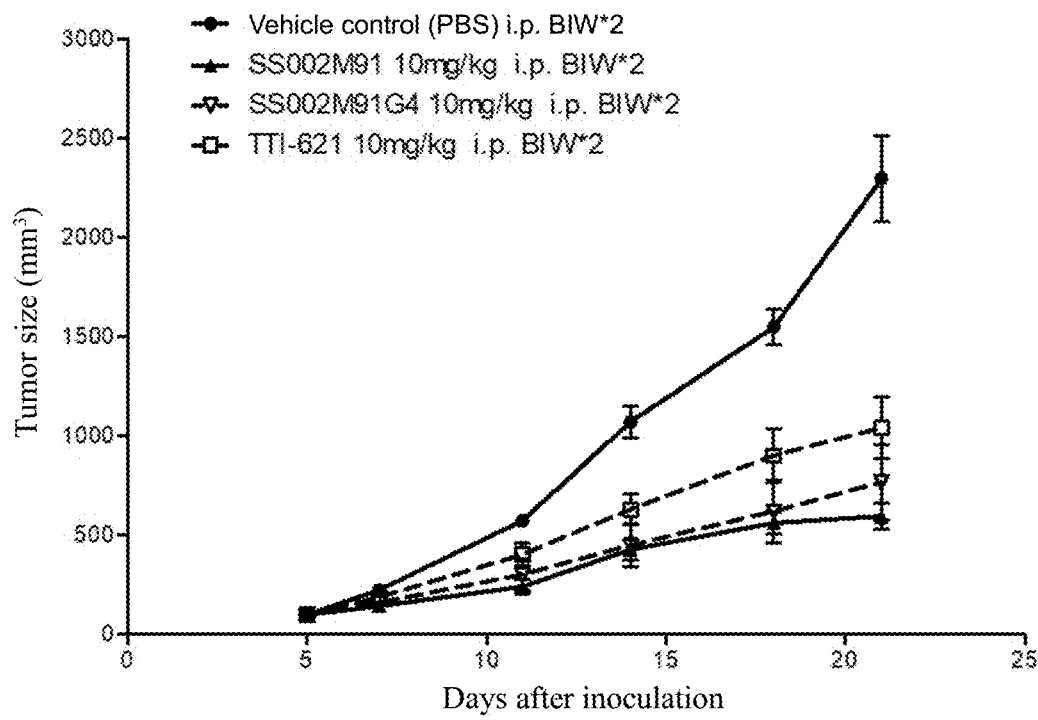
FIG. 19 shows the inhibitory effects of the fusion protein of the present application on the tumor growth in mice.
Figure 20:
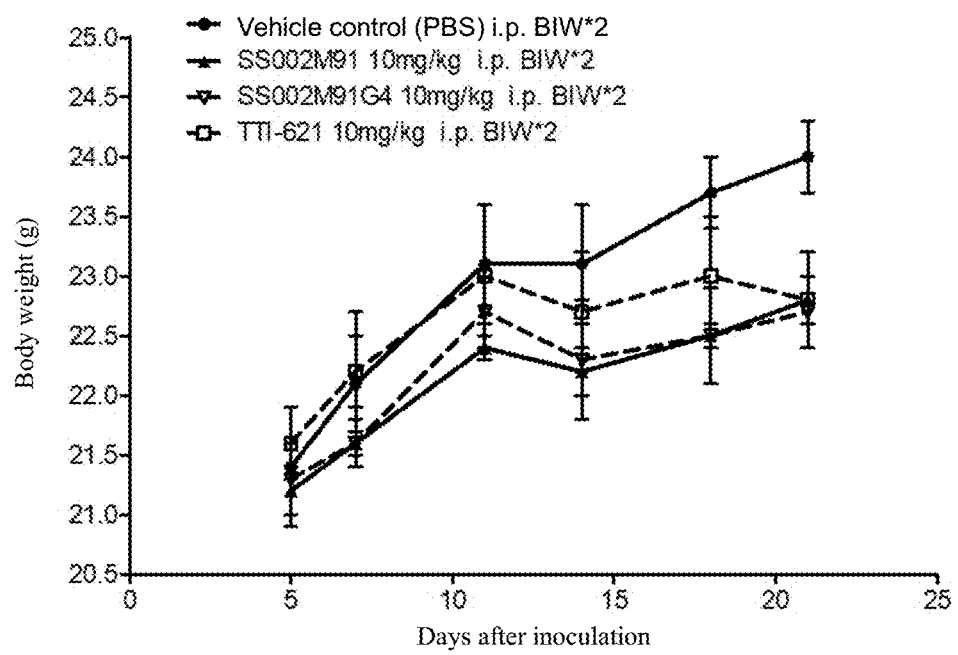
FIG. 20 shows the effects of the fusion protein of the present application on the body weight of mice.

The experiment was ended on Day 6 after the last administration, and blood was taken for routine blood testing. Red blood cells and platelets in peripheral blood of the mice were analyzed for their levels (the level of red blood cells and the level of platelet were shown in FIG. 18A and FIG. 18B, respectively). During administration, the mice were observed for the tumor growth. The therapeutic effect was evaluated in accordance with the relative tumor growth inhibition (TGI) (the results were shown in FIG. 19), and the safety was evaluated based on the weight change of animals and deaths (the results were shown in FIG. 20). The formula for calculating TGI (%), that was, relative tumor growth inhibition was as follows: TGI %=(1−T/C)×100%. Of those, T and C are the relative tumor volume (RTV) or tumor weight (TW) of the treatment groups (e.g., SS002M91 group, SS002M91G4 group and TTI-621 group) and the control group (i.e., the vehicle control group) at a specific point of time.

The results showed that the SS002M91 group, the SS002M91G4 group, and the TTI-621 group (10 mg/kg) all showed a significant tumor inhibition effect on Day 6 after drug withdrawal, and exhibit relative tumor growth inhibitions TGI (%) of 74.09%, 66.65% and 54.75%, respectively. As compared to the vehicle control group, there are statistically significant differences (all the p values are less than 0.01). SS002M91 group and SS002M91G4 group have similar tumor-inhibiting effects and are better than the positive control TTI-621 group.

During the treatment, no animal died or exhibited obvious drug toxicity, and all of them are well tolerated. Routine blood test results showed that as compared with the positive control TTI-621 group, the red blood cells and platelets of the SS002M91 group were reduced, the platelets of the TTI-621 group were also slightly decreased, but the red blood cells were not substantially affected by SS002M91G4.

The foregoing detailed description was provided by way of illustration and examples, and was not intended to limit the scope of the appended claims. At present, various variations of the embodiments as listed herein are obvious to those of ordinary skills in the art, and remain in the scope of the appended claims and their equivalent solutions.

The invention claimed is:

1. A human SIRPα (signal regulatory protein α) domain mutant, wherein the human SIRPα domain mutant comprises an amino acid sequence as set forth in any one of SEQ ID NOs: 2, 3, 10, 11, 12 and 14.

2. A fusion protein, comprising the human SIRPα domain mutant of claim 1.

3. The fusion protein according to claim 2, wherein said fusion protein further comprises an immunoglobulin Fc region, wherein said human SIRPα domain mutant is directly or indirectly linked to the immunoglobulin Fc region.

4. The fusion protein according to claim 3, wherein said immunoglobulin Fc region comprises an Fc region of IgG.

5. The fusion protein according to claim 4, wherein said IgG is selected from the group consisting of IgG1 and/or IgG4.

6. The fusion protein according claim 3, wherein said human SIRPα domain mutant is located at N-terminus of the immunoglobulin Fc region.

7. The fusion protein according to claim 3, wherein said immunoglobulin Fc region comprises an amino acid sequence as set forth in any one of SEQ ID NOS: 67-68.

8. The fusion protein according to claim 2 comprising an amino acid sequence as set forth in any one of SEQ ID NOs: 22, 23, 30, 31, 32, 34, 42, 43, 50, 51, 52, and 54.

9. A composition, comprising the fusion protein according to claim 2, and optionally a pharmaceutically acceptable adjuvant.

* * * * *